US008834404B2

(12) United States Patent
Beaudin

(10) Patent No.: US 8,834,404 B2
(45) Date of Patent: Sep. 16, 2014

(54) APPARATUS, SYSTEM AND METHODS FOR EXTRACORPOREAL BLOOD PROCESSING FOR SELECTIVELY COOLING THE BRAIN RELATIVE TO THE BODY DURING HYPERTHERMIC TREATMENT OR TO INDUCE HYPOTHERMIA OF THE BRAIN

(75) Inventor: Steve Andre Beaudin, Nepean (CA)

(73) Assignee: Steve Andre Beaudin, Ottawa (CA)

( * ) Notice: Subject to any disclaimer, the term of this patent is extended or adjusted under 35 U.S.C. 154(b) by 60 days.

(21) Appl. No.: 13/262,410

(22) PCT Filed: Mar. 30, 2010

(86) PCT No.: PCT/CA2010/000471
§ 371 (c)(1),
(2), (4) Date: Sep. 30, 2011

(87) PCT Pub. No.: WO2010/111778
PCT Pub. Date: Oct. 7, 2010

(65) Prior Publication Data
US 2012/0029408 A1    Feb. 2, 2012

Related U.S. Application Data

(60) Provisional application No. 61/164,713, filed on Mar. 30, 2009.

(51) Int. Cl.
*A61M 37/00* (2006.01)
*A61M 1/00* (2006.01)
*A61M 1/36* (2006.01)

(52) U.S. Cl.
CPC ......... *A61M 1/369* (2013.01); *A61M 2205/366* (2013.01); *A61M 2205/3606* (2013.01)
USPC ........................................ 604/6.13; 604/4.01

(58) Field of Classification Search
CPC ............ A61F 7/00; A61F 7/12; A61M 1/369; A61M 5/44
USPC ................ 604/4.01–6.16; 607/104–106, 113; 422/44–48
See application file for complete search history.

(56) References Cited

U.S. PATENT DOCUMENTS 6,669,661 B1 * 12/2003 Yee .............................. 604/6.13

FOREIGN PATENT DOCUMENTS

WO    WO 2005117546 A2 * 12/2005

* cited by examiner

*Primary Examiner* — Philip R Wiest
*Assistant Examiner* — Benjamin Klein

(57) ABSTRACT

A system, apparatus and methods are provided for extracorporeal blood treatment, and in particular for establishing and maintaining a neck down differential body temperature, while maintaining near normal brain temperatures, to protect the brain from extended or extreme hypothermia or hyperthermia. A blood treatment apparatus and system is provided for differential control of brain temperature and body temperature below the neck. For example, a first bypass circuit with heat exchanger for brain blood circulation maintains a near normal blood temperature, while a second bypass circuit for below the neck blood circulation provides for thermal treatment to induce a temperature differential, e.g. hyperthermia or hypothermia, relative to brain circulation. Such systems and apparatus have application, for example, for diagnostic and therapeutic treatments using hyperthermia, particularly for treatments of extended duration or at elevated temperatures above 42° C., for example, hyperthermia for treatment of cancer, infectious bacterial or viral diseases.

44 Claims, 16 Drawing Sheets

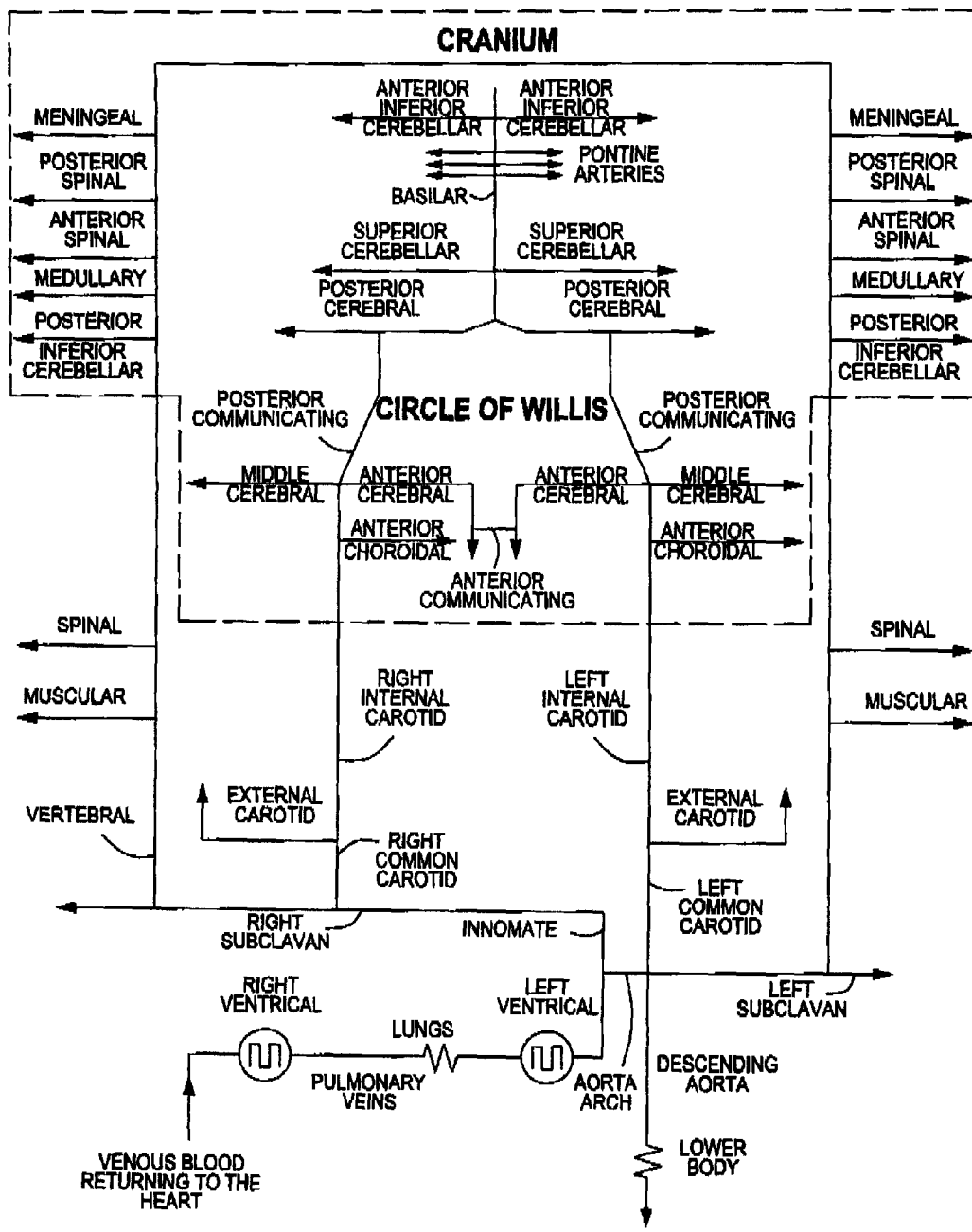
Figure 1: Arterial Schematic of Neck and Brain

Figure 2: Circle of Willis
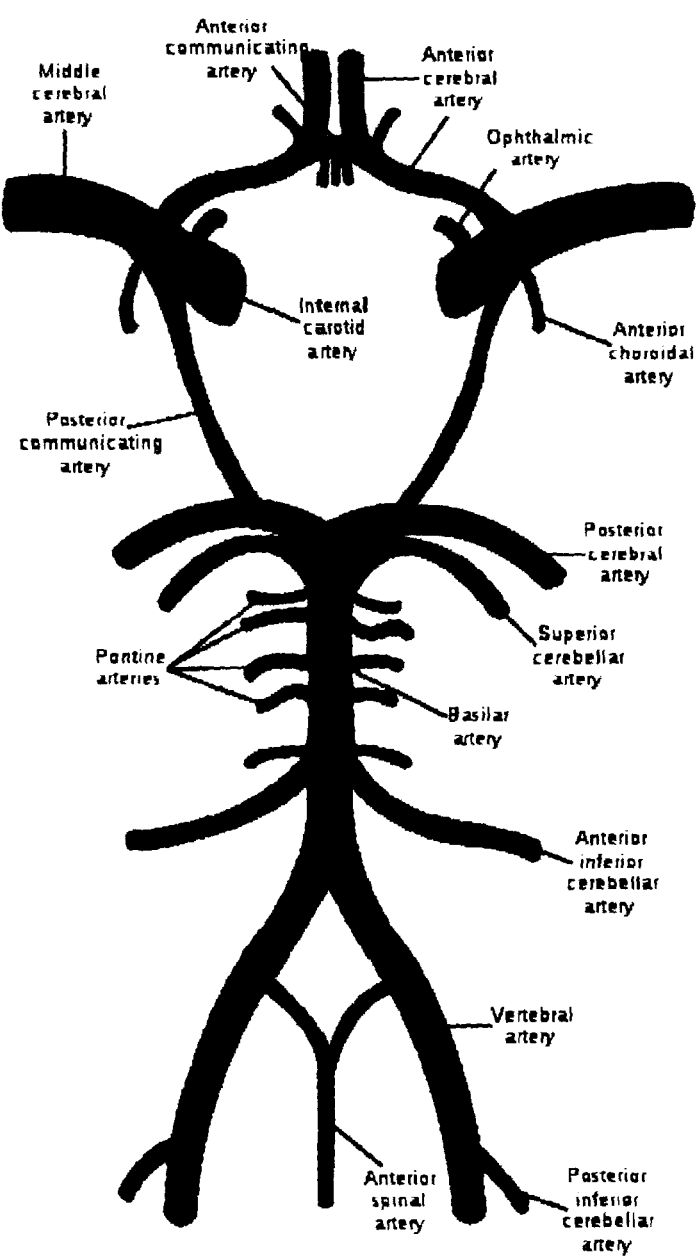

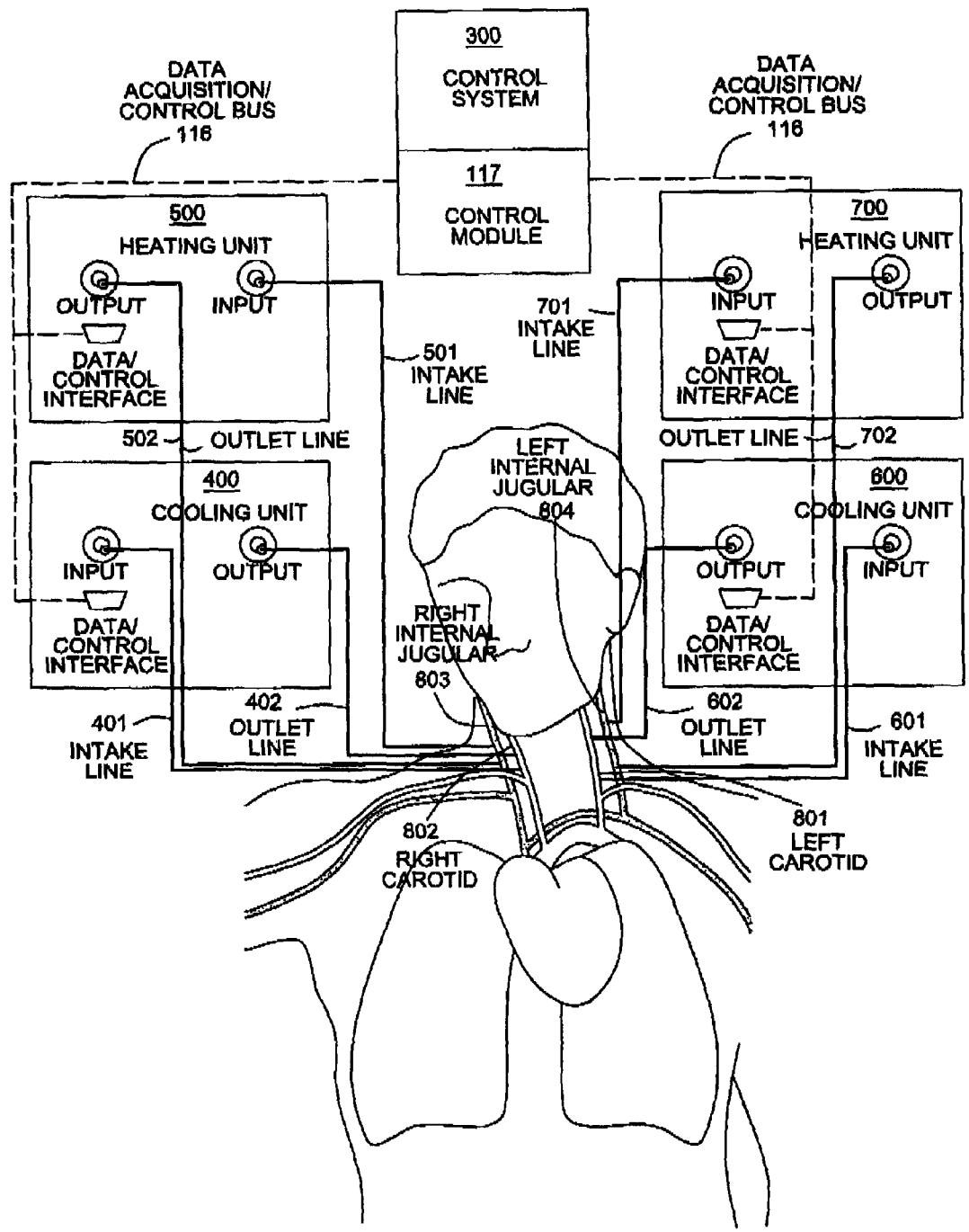
Figure 3: System Setup when all Arterial and Venous Catheters are connected to the neck.

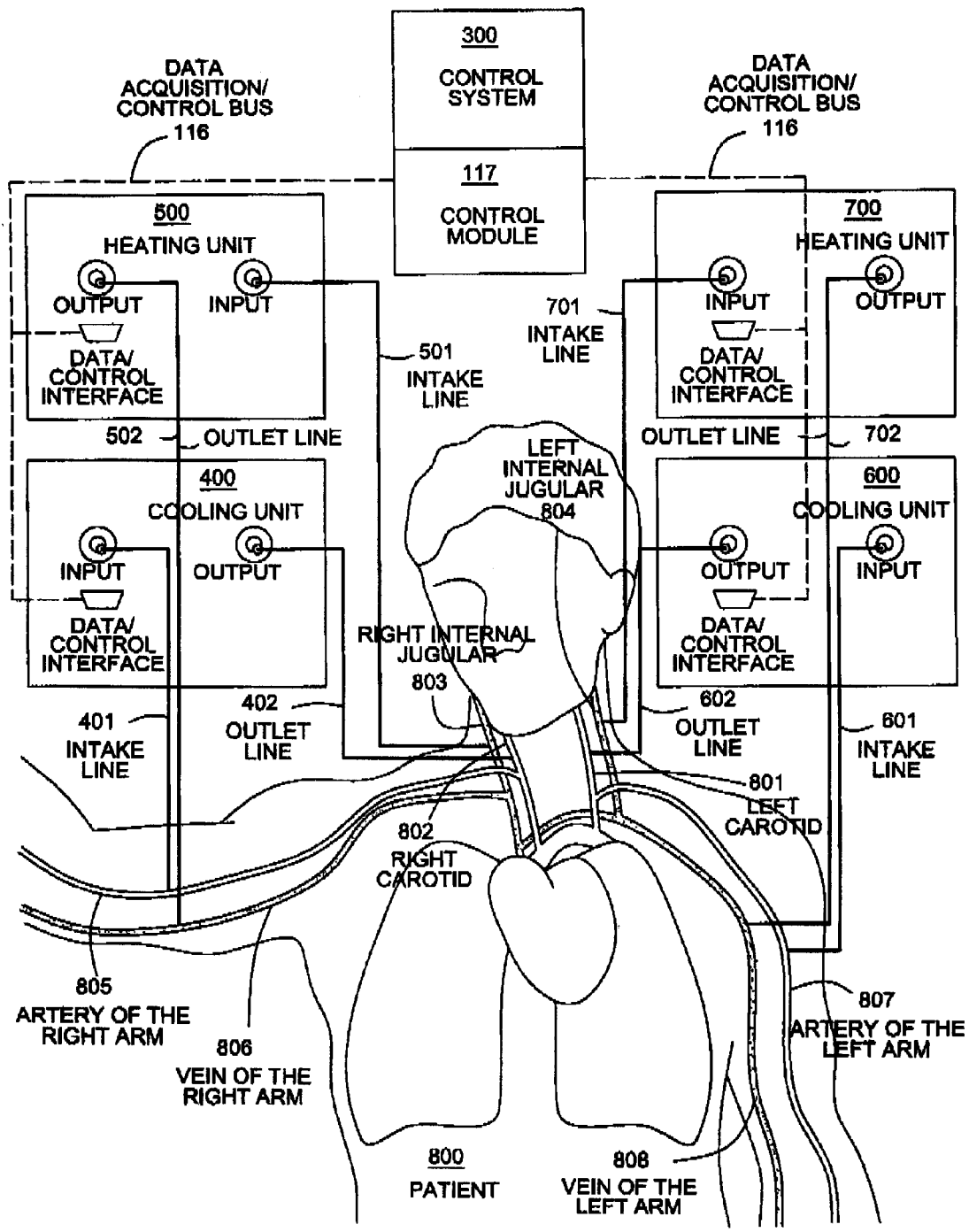
Figure 4: System Setup when the bypass circuit comprises 1 catheter in an arm and 1 catheter in the neck.

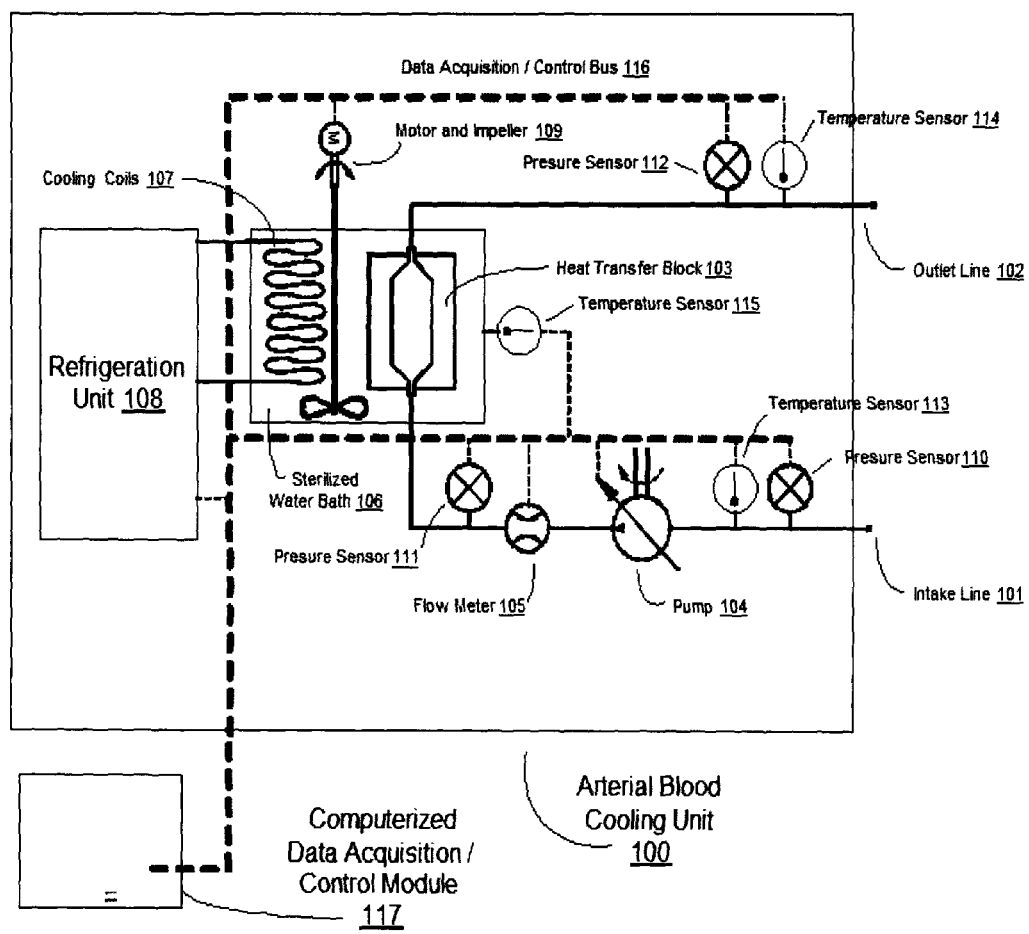
Fig. 5: ExtraCorporeal Cooling Unit

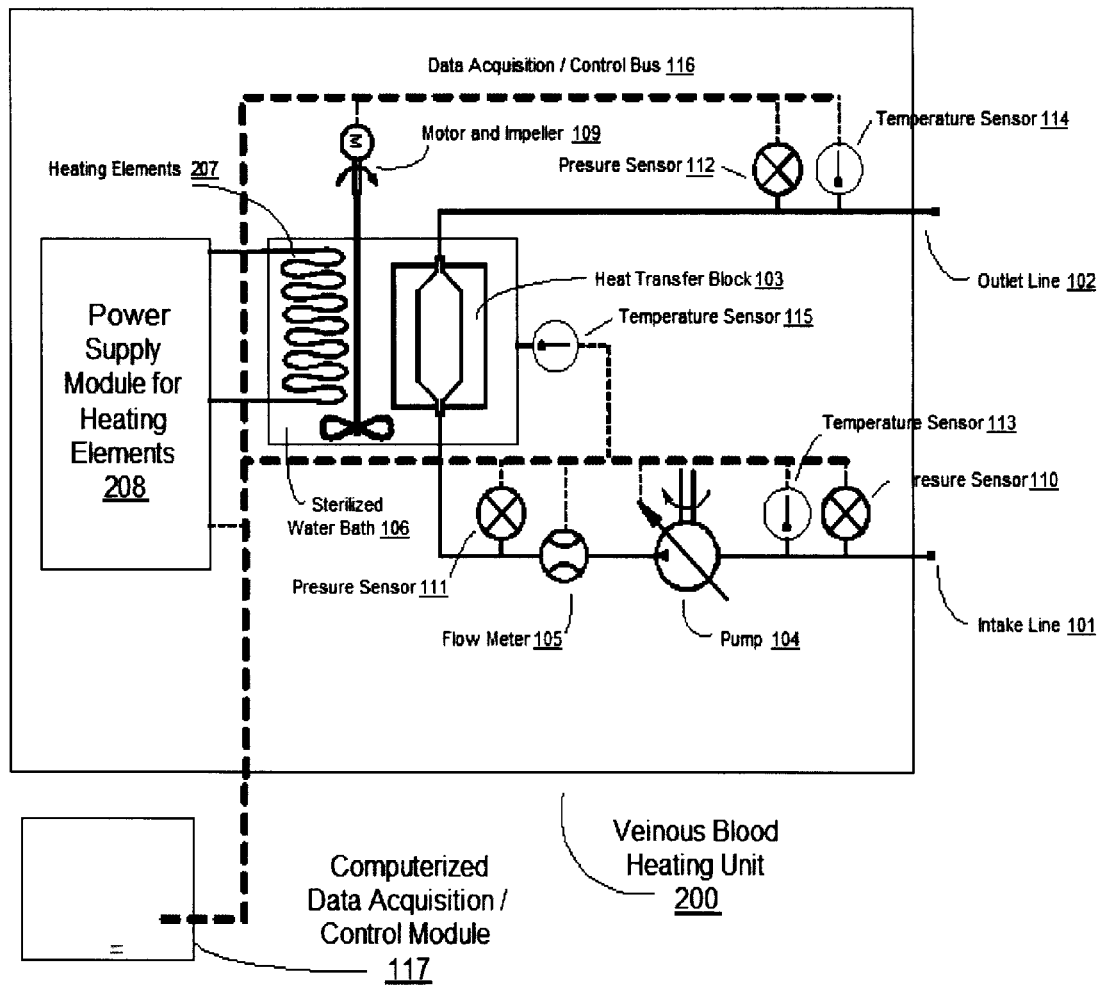
Fig. 6: ExtraCorporeal Heating Unit

Preferred Embodiment A
Figure 7: Key Temperatures
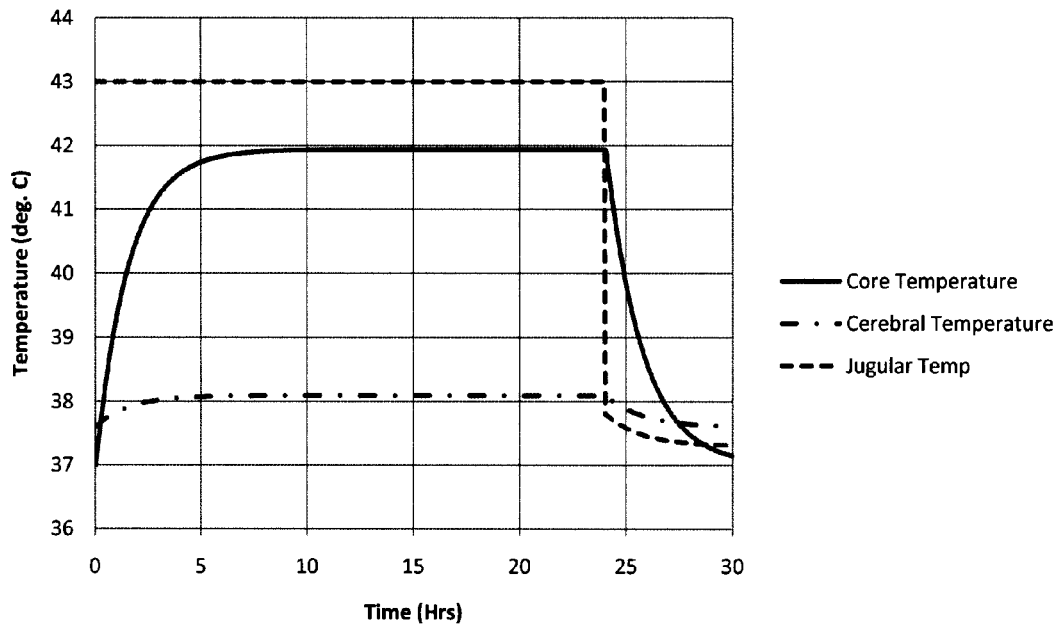
Figure 8: Heat Transfer Parameters
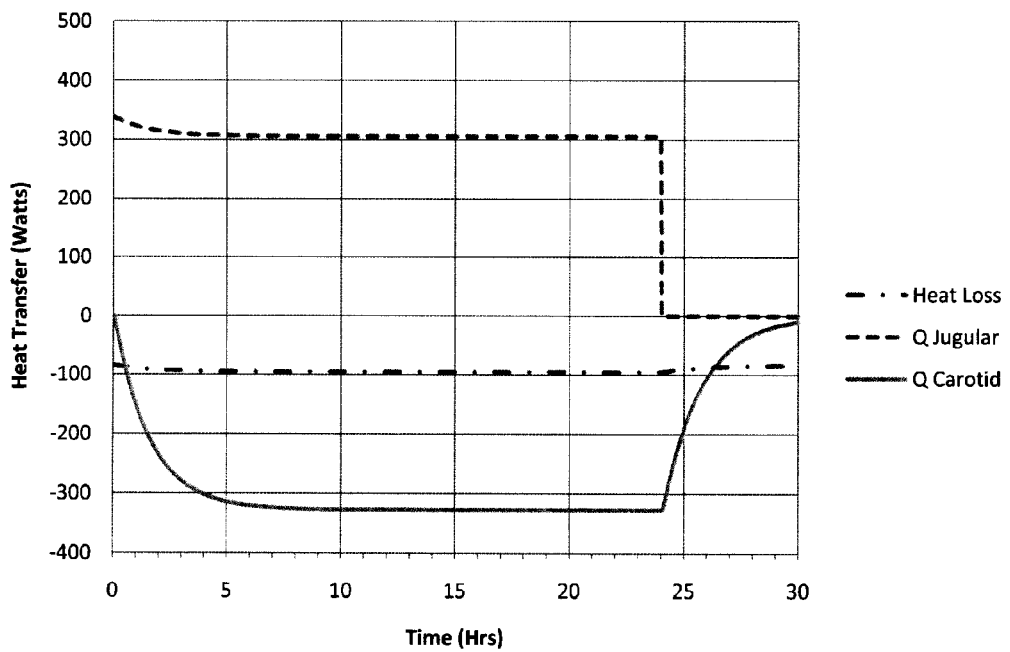

Preferred Embodiment B
Figure 9: Key Temperatures
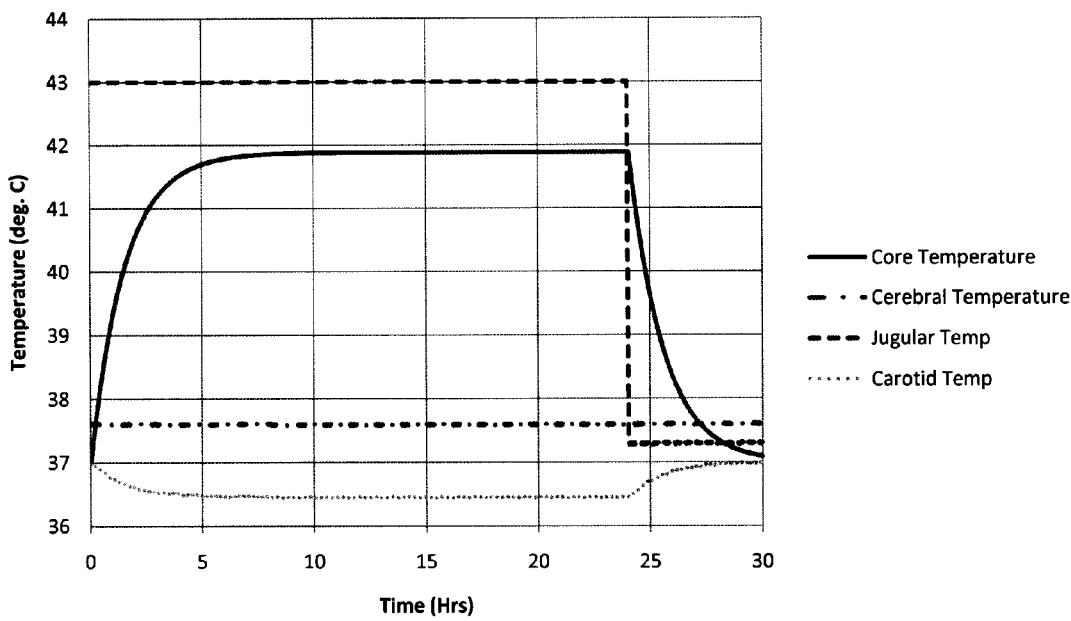
Figure 10: Heat Transfer Parameters
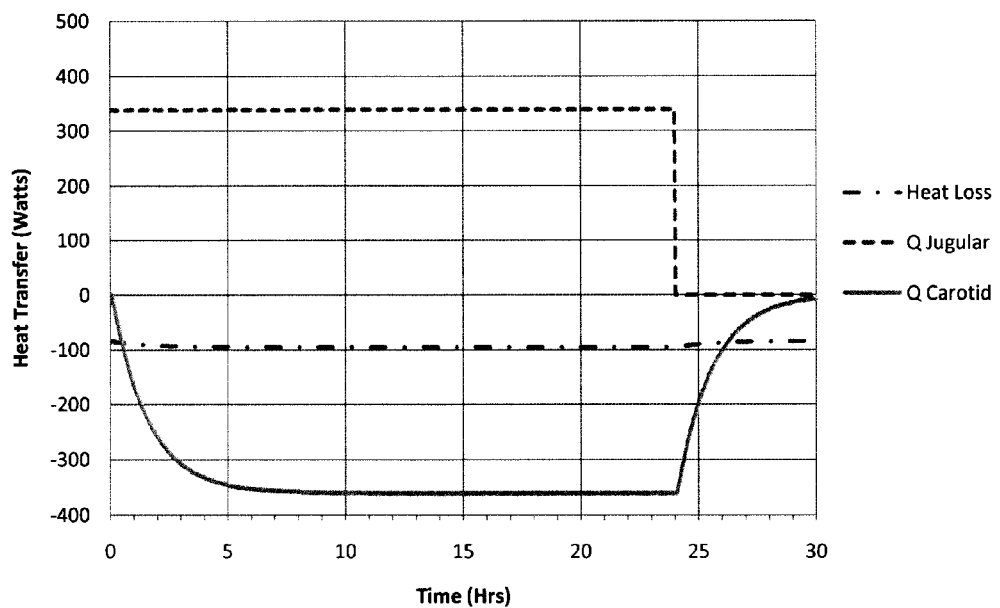

Preferred Embodiment C
Figure 11: Key Temperatures
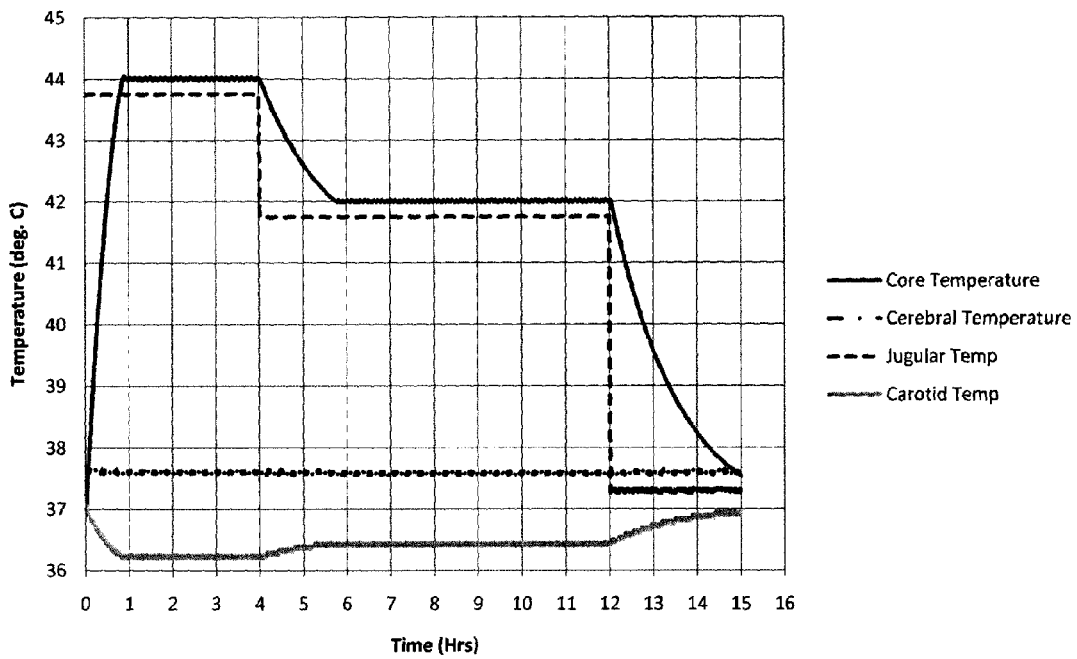
Figure 12: Heat Transfer Parameters
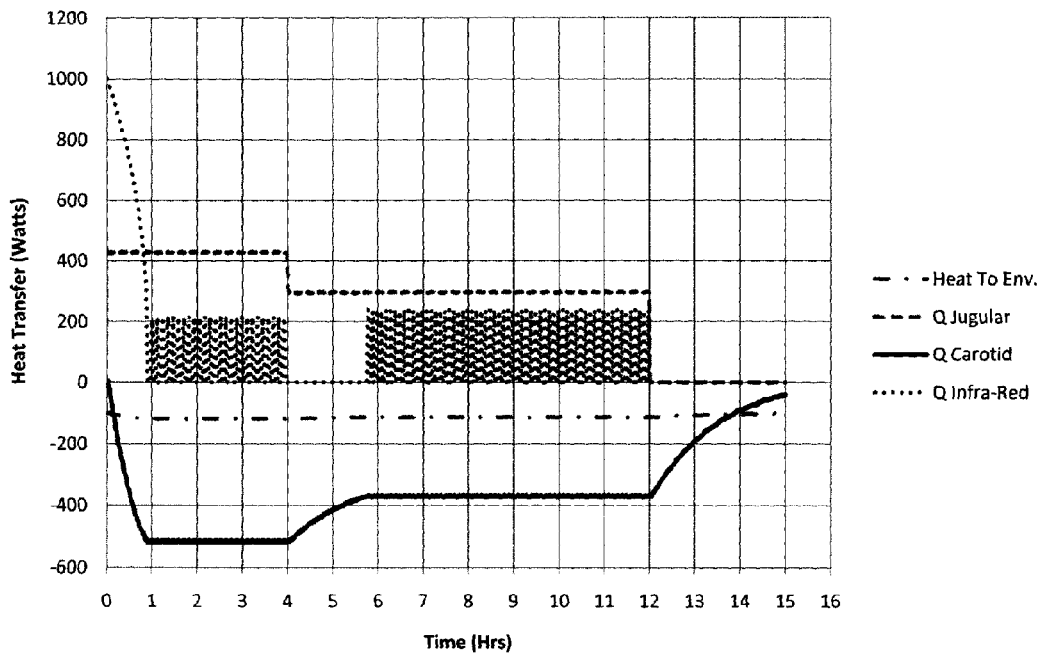

Preferred Embodiment D
Figure 13: Key Temperatures
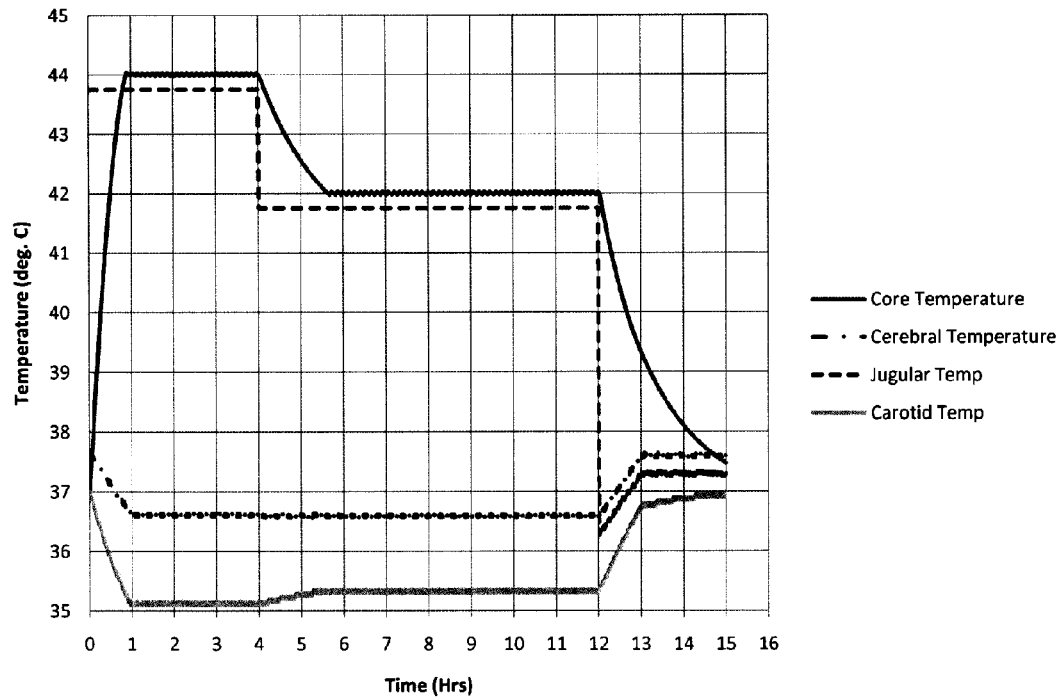
Figure 14: Heat Transfer Parameters
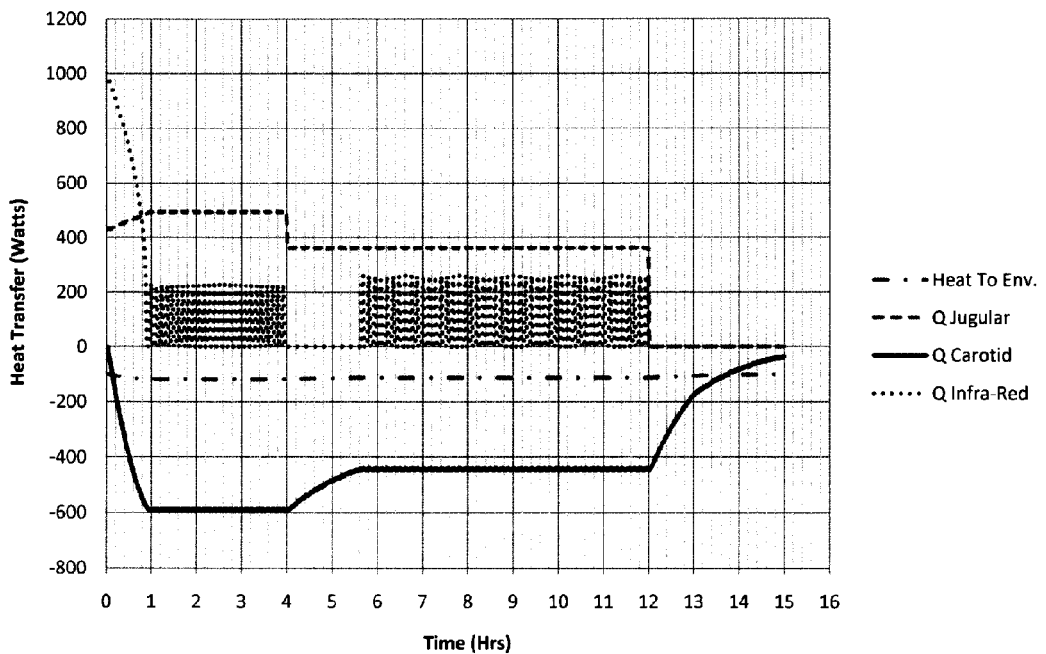

Preferred Embodiment E
Figure 15: Key Temperatures
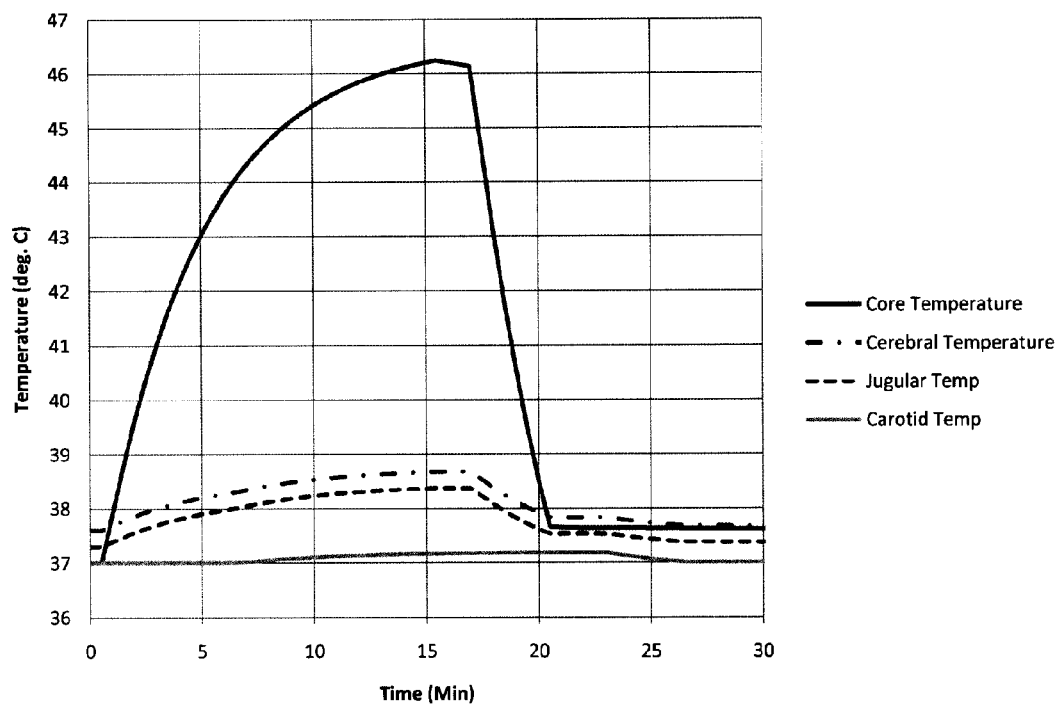
Figure 16: Heat Transfer Parameters
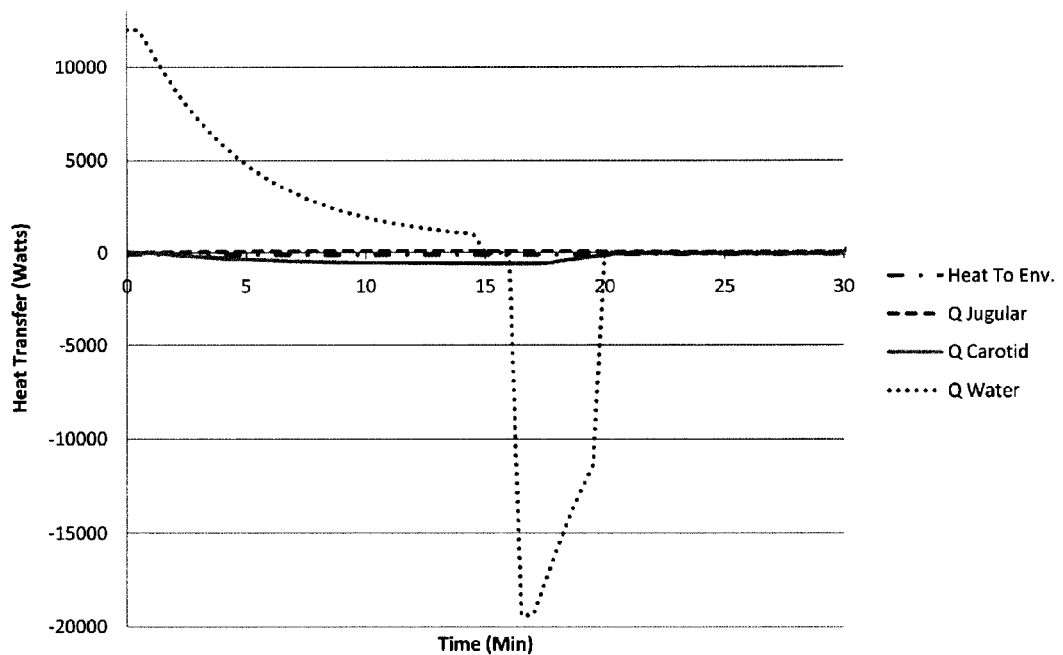

Preferred Embodiment F
Figure 17: Key Temperatures
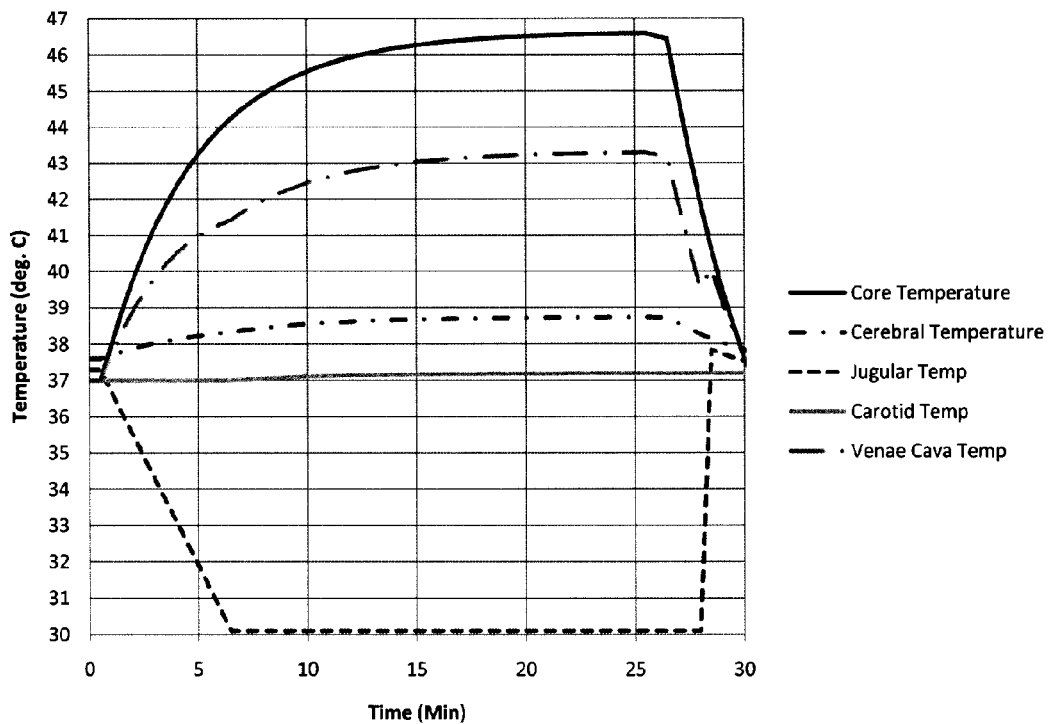
Figure 18: Heat Transfer Parameters
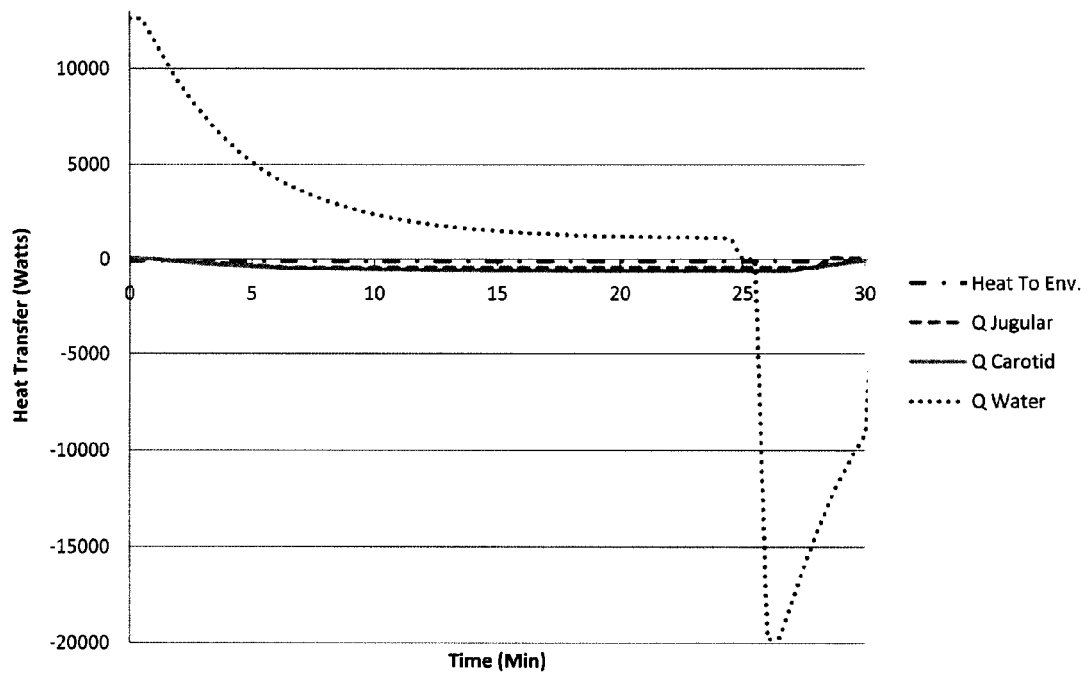

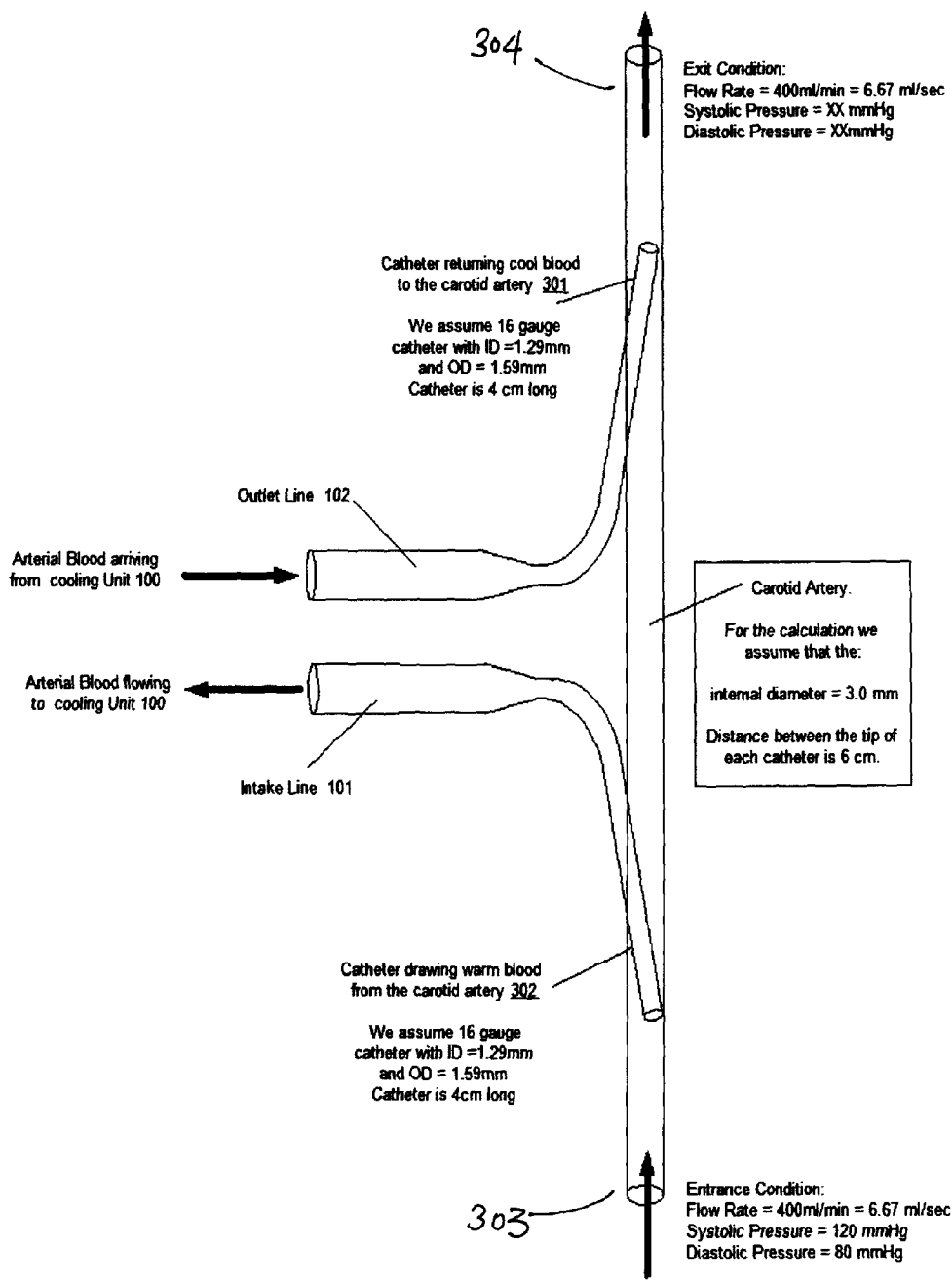
Figure 19: Catheter Placement in Carotid Artery, Fluid Mechanics Considerations

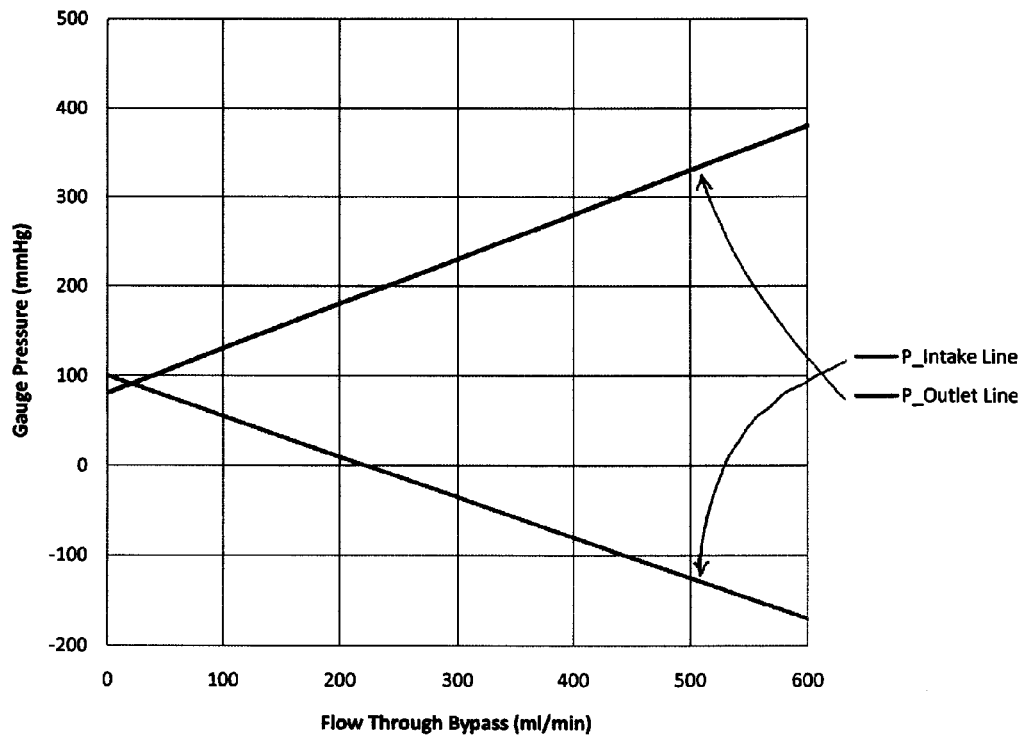
Figure 20: Pressure on Intake and Outlet Line
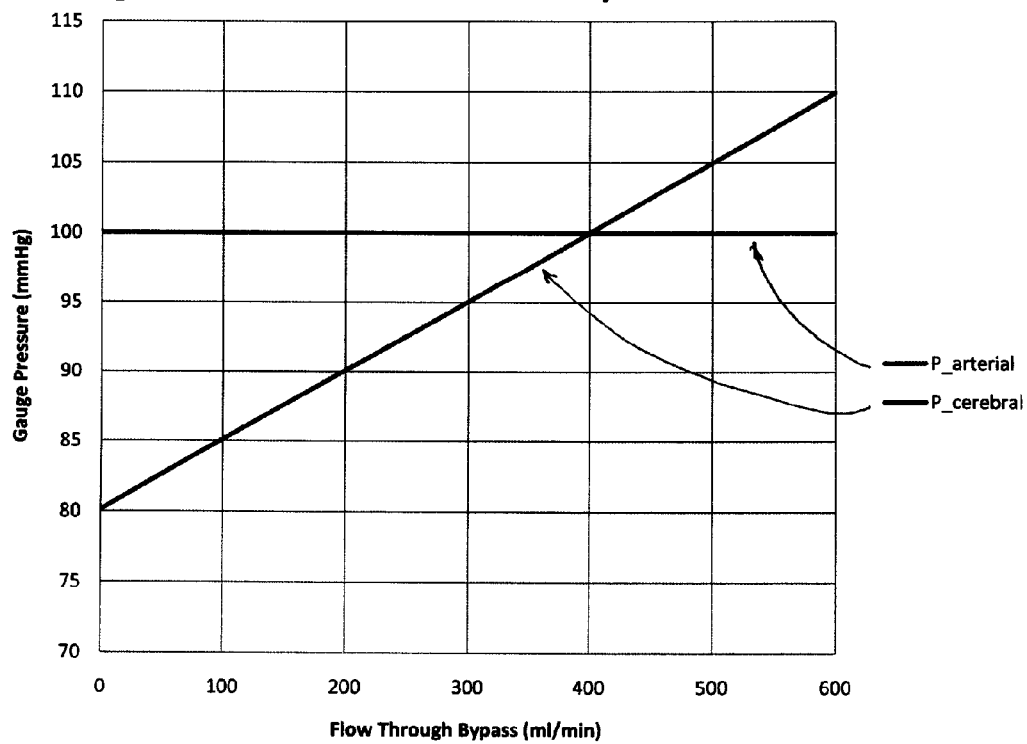
Figure 21: Arterial Pressure vs. By-Pass Flow Rate

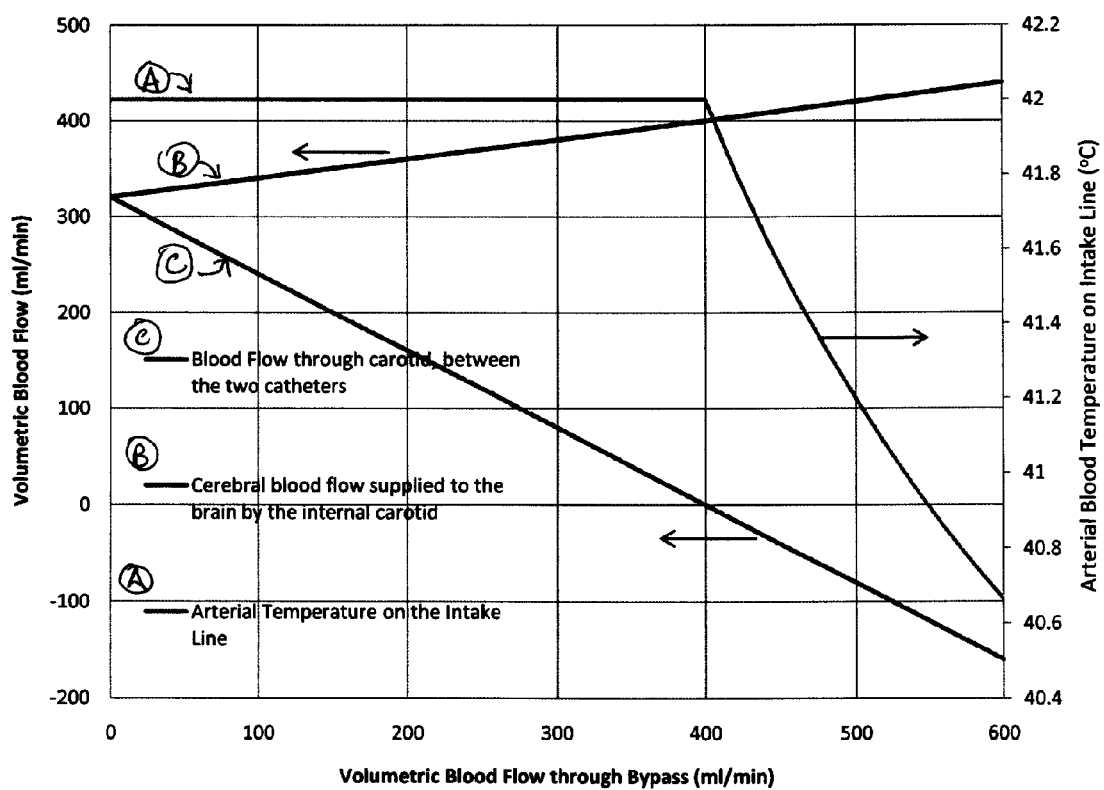
Figure 22: Blood Flow

Figure 23 Cross Section of Heat Transfer Block
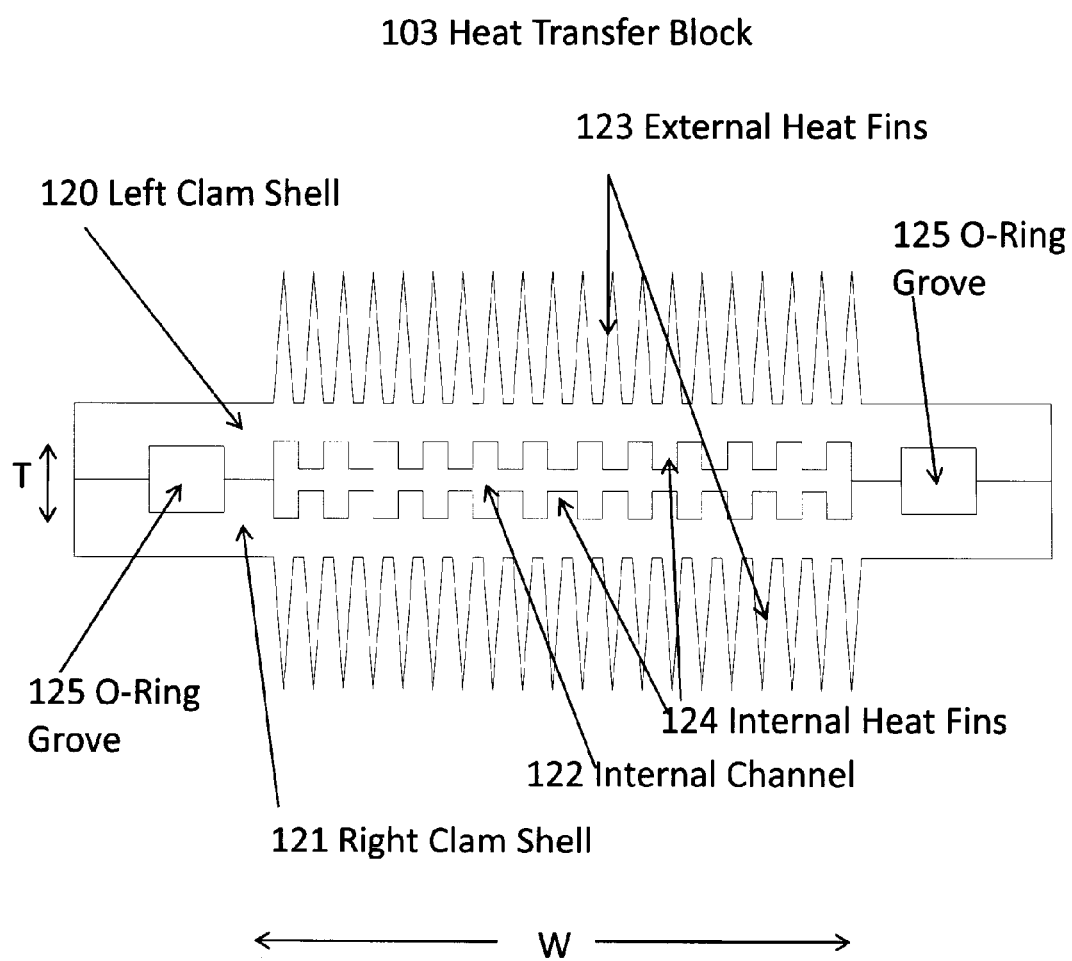

APPARATUS, SYSTEM AND METHODS FOR EXTRACORPOREAL BLOOD PROCESSING FOR SELECTIVELY COOLING THE BRAIN RELATIVE TO THE BODY DURING HYPERTHERMIC TREATMENT OR TO INDUCE HYPOTHERMIA OF THE BRAIN

CROSS REFERENCE TO RELATED APPLICATIONS

This application claims priority from U.S. Provisional Application No. 61/164,713 filed Mar. 30, 2009, entitled "Neck Down Induced Hyperthermia with bypass cooling to the brain, for the treatment of Cancer, HIV and other Diseases", which is incorporated herein by reference.

TECHNICAL FIELD

The invention relates to the field of induced hyperthermia or hypothermia for medical treatment and diagnostic purposes. The invention more particularly relates to bio-medical apparatus, systems and methods for extracorporeal blood processing and for establishing and maintaining an elevated body temperature for hyperthemia treatment of Cancer, HIV and other diseases.

BACKGROUND ART

Normal human body temperature, also known as normothermia or euthermia, depends upon the place in the body at which the measurement is made, and the time of day and level of activity of the person. Different parts of the body have different temperatures. Measurements taken directly inside the body cavity are typically slightly higher than oral measurements, and oral measurements are somewhat higher than skin temperature. A commonly accepted average core body temperature (taken internally) is 37.0 C (98.6° F.). A typical oral (under the tongue) measurement is 36.8±0.7 C, or 98.2±1.3 F.

The use of intentional cooling to reduce body temperature, which creates a state of hypothermia, has application, for example, to slow metabolic processes and reduce oxygen demand, which can be beneficial during medical procedures, such as heart surgery.

The use of heat to create an elevated body temperature, i.e. hyperthermia, as a means of treating cancer and other diseases has been known and studied since ancient time. More recently, hyperthermia has been reported to be beneficial in treatment of a number of conditions, including: cancer, HIV/AIDS, Hepatitis C, chronic inflammatory conditions such as ulcerative colitis and Crohn's disease, rheumatic conditions, bronchial asthma, chronic and recurrent viral infections, conditions requiring detoxification, and herpes simplex virus.

Global interest in hyperthermia as a means of treating cancer was initiated by the first International Congress on Hyperthermic Oncology in Washington in 1975. In the last several decades hyperthermia has been shown to be an effective means of treating cancer either stand alone or in conjunction with other treatments such as radiotherapy or chemotherapy.

The fact that in vivo tumour cells are more sensitive to heat than normal healthy cells has been well established [1,2]. A tumour cell killing effect is achieved at temperatures between 40 and 44 Celsius. At temperatures above 42.5-43° C. the exposure time can be halved with each 1° C. of temperature increase to give an equivalent cell kill [2]. Most normal cells and tissues are undamaged by treatment of up to 44° C. for 1 hour [3].

Hyperthermia can be induced in several different ways. Local hyperthermia can be induced by external or internal energy sources. Regional hyperthermia can be achieved by perfusion of organs or limbs or by irrigation of body cavities. Whole body hyperthermia can also be induced in patients whose cancer has spread to several different areas.

The effectiveness of hyperthermia treatment is related to the temperature achieved during the treatment, as well as the length of treatment and cell and tissue characteristics. Normal tissues are generally not damaged during hyperthermia if the temperature remains under 111° F. or 44° C. It is therefore beneficial to raise the temperature of the tumour as high as possible while limiting the temperature of surrounding healthy tissues to 44° C. or lower.

Local Hyperthermia:

With local hyperthermia, an energy source causes the temperature of a tumour to be heated and rise locally. For local hyperthermia there is little heat rise for tissues at some distance from the tumour. However, it is difficult to ensure that the entire tumour is being exposed to sufficiently high temperatures without overheating the surrounding tissues. Furthermore, if parts of the tumour are not sufficiently heated, then some cancer cells survive the treatment and they continue to multiply.

Regional Hyperthermia:

Regional hyperthermia heats a part of the body, such as an organ, limb, or body cavity. It is generally combined with chemotherapy or radiation therapy. One approach, called regional perfusion, isolates the blood supply for that part of the body and uses a heating device to warm the blood and pump it back into the area to heat it. This method is being studied to treat certain cancers in the arms or legs.

A similar technique is being tested along with surgery against cancers in the abdominal cavity. During surgery, heated chemotherapy drugs are circulated through the peritoneal cavity. This is called continuous hyperthermic peritoneal perfusion, or CHPP.

Yet another approach to regional hyperthermia is deep tissue hyperthermia. This method uses RF or Microwave radiating devices that are placed on the surface of the organ or body cavity and produce high energy waves directed at a specific area.

Whole Body Hyperthermia:

Whole body hyperthermia is also being studied as a way to make chemotherapy more effective in treating cancer that has spread (metastatic cancer). Body temperature is raised by using warm-water blankets, inductive coils (like those in electric blankets), or thermal chambers (much like large incubators).

Moderate Whole Body Hyperthermia stimulates the immune system. By raising the core body temperature to approximately 39.5° C. (103.1 F) a natural fever is simulated which in turn increased the number and activity of natural cells, T-helper cells and cytotoxic T-cells. This treatment is also used in cancer diseases with special association to the immune system like renal-cell-carcinoma, malignant melanoma and special lymphomas. This method can also be used to prevent recurrences.

Extreme whole body hyperthermia is used in a combination with chemotherapy in advanced or metastatic cancer. The body core temperature is increased up to 42° C. (107.6 F). This method is useful in advanced cancer, especially with metastases of different organs, e.g. in the liver, bones or lungs.

In combination with whole body hyperthermia, chemotherapy has been demonstrated to be more effective. The chemotherapy is started at a temperature of about 41° C. (105.8 F). Often, when combined with hyperthermia, it is possible to use very low doses of chemotherapy so side effects are kept to a minimum. Tumours or metastases resistant to chemotherapy can be successfully treated with a combination treatment of chemotherapy and whole body hyperthermia.

Hyperthermia as a Treatment for HIV/AIDS

Hyperthermia has also been studied and found to have some effectiveness in treating HIV and AIDS and potentially other infectious diseases where the virus or bacteria is sensitive to elevated temperatures. Several studies have been performed over the last decade which showed that Whole Body Hyperthermia was a promising means of treating HIV.

For example, Alonso reported the long-term results of a single session of low-flow (0.3 L/min) extracorporeal perfusion hyperthermia on 29 men and 2 women with disseminated Kaposi's sarcoma and profound immunologic impairment [4]. Antiretroviral treatment was stopped 72 hours prior to treatment and withheld during the period of follow-up. Core temperature was raised to 42 Celsius and held for 1 hour with extracorporeal perfusion and ex vivo blood heating to 49 degrees C. as the means of temperature control. Of 31 patients, 2 died of complications secondary to treatment (cardiac arrhythmia; CNS bleeding). There were two cases of intravascular coagulopathy. At 30 days post-treatment complete or partial regressions were seen in 20/29 of those treated, with regressions persisting in 14/29 of those treated by 120 days post treatment. At 360 days, 4/29 maintained tumour regressions with 1 in complete remission (at 26 months). The patient in complete remission remained culture-negative and PCR-negative for HIV and his CD4 count rose from around 250 to around 800. Selected healed lesions were biopsied to demonstrate tumour absence. Patients were selected for treatment if pre-treatment testing of the tumour showed regression in vitro with heat exposure. Analysis of the early and midterm failures showed little sustained rise of the CD4 cells if presenting total CD4 counts were below 50 and had been at such low levels for extended periods. Analysis of the tumours of the few men not responding demonstrated elevated levels of IL-6 as compared to responders (12 vs. <1 pg/ml). At 120 days 29/31 patients remained alive (expected, 20). At 360 days, 21/31 remained alive (expected, 11). In no patient was HIV activity stimulated with heat exposure. It was noted by Alonso et al. that the effectiveness of the hyperthermia to boost CD4+ lymphocytes was not significant in patients with significant immunodeficiency and very low CD4 counts while for patients which retained relatively high CD4 of 300 or greater, a significant increase was observed post treatment.

In the clinical trial conducted by Alonso and colleagues, hyperthermia was induced by using a low flow (0.3 L/min) extracorporeal perfusion heating method. A perfusion catheter was inserted into the femoral artery and vein of the opposing limb. Blood flow was propelled by the patient's own arterial pressure, to a roller pump, and was heated by a heating block to 49° C. before being reinserted into the femoral vein. Blood, rectal and intramuscular thermometers monitored patient temperatures.

Steinhart later engaged in an FDA-approved trial of hyperthermia as a means of treating HIV. Steinhart enrolled six men with CD4 counts below 200 and at least three KS lesions in the first FDA-approved trial of hyperthermia. Participants underwent one hour of whole-body hyperthermia at 40 or 42 degrees Centigrade. No adverse side-effects were observed during treatment. KS lesions partially regressed immediately following whole-body hyperthermia in all participants but returned to pre-treatment status in five people after one week. Participants experienced a significant reduction in HIV RNA immediately after cool-down in the 42 degree Centigrade treatment group which returned to pre-treatment levels after one week.

There is also a reasonably large body of research which has established the sensitivity of the HIV virus to temperature. HIV, like other enveloped viruses is temperature-sensitive and suffers greater inactivation for a given length of time as temperatures progressively increase above 37° C. [5]. Spire et al. demonstrated a 40% inactivation of HIV when maintained in a warm water bath for 30 minutes [6]. McDougal et al. demonstrated a linear log relationship of HIV kill from 37° C. to 56° C. [7]. Marcial-Vega et al. demonstrated that a 2-hour exposure of HIV to 42° C. effectively killed all free virus (to concentrations of 800 ng/ml) as well as infected cells [8]. Wong et al. found that HIV-infected cells are more sensitive to heat damage that uninfected cells and that this sensitivity was potentiated by tumour necrosis factor-a. A secondary benefit of whole body hyperthermia is the stimulation of antibody production following an elevated core body temperature [9,10]. This is potentially why CD4 counts increased following whole body hyperthermia in the Alfonso study, in patients which had an initial CD4 counts still about 200.

Based on the work cited above it seems that heat or hyperthermia is a promising approach to treating HIV. Preliminary work using whole body hyperthermia has demonstrated an ability to slow down the progression of AIDS and extend patient life, although as of yet there does not seem to be any reported cases where the virus was totally eradicated. Furthermore, a large body of work which aims to study the temperature sensitivity of HIV to temperature has shown that temperatures which are within range of whole body hyperthermia, i.e. 42° C., effectively killed all free virus as well as infected cells [8].

There is also a growing body of work which aims to leverage whole body hyperthermia for the treatment of hepatitis C. In 2002, the Netherlands Liver Foundation (NLF) initiated a clinical trial to evaluate whole body hyperthermia as a means of treating hepatitis C. The trial was conducted at the Utrecht Medical Centre in Hepatology. The rational for using whole body hyperthermia for treating hepatitis C are similar to HIV. The elevated temperatures preferentially kill HVC virus and a secondary benefit is achieved since, as discussed above, hyperthermic temperatures have been shown to stimulating the immune system.

Other Diseases

It should also be noted that hyperthermia could also be used to treat other diseases. Any infectious disease where the pathogen is found to be adversely affected by elevated temperature could potentially be treated by hyperthermia. Furthermore, given that the immune system is stimulated by an elevated core body temperature, a secondary benefit could be produced even for infectious diseases which are not sensitive to temperature.

Thus in summary, it has been shown that whole body hyperthermia could be induced up to temperatures of about 42° C. Core body temperatures of up to 42° C. or in some cases as low as 39° C. were found to be effective at treating cancer, HIV, Hepatitis C and other infectious or chronic diseases. Much research has been performed on using hyperthermia as a treatment for cancer, while its use for HIV treatment is a fairly new area which has shown some promising results. Hyperthermia has also been used to treat chronic inflammatory conditions such as ulcerative colitis and Crohn's disease, rheumatic conditions, bronchial asthma, chronic and recurrent viral infections and even conditions requiring detoxification.

Nevertheless, it is also known that during hypothermic or hyperthermic procedures, the brain is more sensitive to changes in temperature than most other parts the body. While in some circumstances, the brain has been found to withstand an extended period of hypothermia, as low as 30° C., i.e. about 7° C. below normal body temperature, it is also well known that the brain is much less able to withstand similar temperature differentials above normal, or even extended periods of hyperthermia above 42° C., without risk of significant damage or life-threatening effects. Studies have shown that the human brain begins to show damage when the core temperature reaches 41° C. Damage to the brain, as well as the physiological response induced by the hypothalamus, are key limitations to raising human body temperature above 42° C.

Thus, during hyperthermic treatment for cancer, HIV or other conditions, it is desirable to protect the patient's brain from detrimental effects of hyperthermia.

By way of example, systems for whole body thermotherapy are disclosed, in U.S. Pat. No. 5,817,045 to Sever, entitled "Apparatus and method for enabling extracorporeal therapy of up to at least one half of a living patient's entire circulating blood supply during a continuous time interval" and in U.S. Pat. No. 5,074,838 to Kroyer et al. entitled "Extracorporal thermo-therapy device and method for curing diseases using penetrants."

U.S. Pat. No. 7,241,307 to Lennox, entitled "Method and Apparatus for Managing Temperature in a Patient" discloses localized cooling of the head for hypothermia treatments only, e.g. for treating brain injury, stroke, or during cardiac arrest, using a single catheter system to withdraw, cool and then reinject a portion of blood in a reciprocating fashion, providing limited temperature control. For elevated hyperthermia treatment as described above, such as system would be problematical, because heated blood flow from the body would enter the brain directly during the intake stroke of the pump, with potentially detrimental effects.

U.S. Pat. No. 6,669,661 to Yee entitled "Method and device for central nervous system protection during whole body hyperthermia or hypothermia", for example, discloses a system and method that attempts to address the problem of protecting the brain and nervous system from the effects of hyperthermia. Not only is this system complex and expensive, but the procedure involves anaesthesia and complete separation CNS circulation from the rest of the body, with associated risks to the patient.

For prolonged hyperthermic treatments, it is desirable to avoid such extreme intervention, and, for example, enable treatment of a conscious patient with minimal disruption of normal blood circulation, while protecting the brain from excessive temperatures.

Thus improved apparatus, systems and methods are required for extracorporeal blood processing for establishing and maintaining hyperthermia for diagnostic and therapeutic treatments.

The present invention seeks to overcome, or at least ameliorate, one or more of the disadvantages of known apparatus, systems and methods, or at least provide an alternative.

DISCLOSURE OF INVENTION

One aspect of the invention provides a method for hypothermic treatment characterized by: subjecting the body to a temperature above a normal core body temperature from the neck down for a therapeutic purpose, while maintaining the brain at a temperature lower than the neck down hyperthermic treatment temperature.

Preferably, the method comprises extracorporeally cooling blood flowing from the body to the brain via at least one carotid artery, and extracorporeally heating blood returning from the brain to the body via at least one jugular vein, for example via suitable extracorporeal circulatory bypass systems with cooling and heating units, respectively. Preferably, the method provides for maintaining vascular pressure in the internal carotid arteries sufficient that the cooled carotid artery flow to the brain is delivered, via the Circle of Willis, to areas of the brain supplied by vertebral and basilar arteries.

Another aspect of the invention provides a method for hypothermic or hyperthermic (thermotherapy) treatment characterized by:
heating or cooling at least part of the body to a core body temperature above or below a normal body temperature from the neck down, while maintaining the brain at a relatively normal temperature, wherein the method is characterized by:
"
diverting blood flow from the heart to the brain via the carotid artery through a extracorporeal circulatory bypass system comprising a heat exchanger warming or cooling the blood flow to a target temperature,
returning warmed or cooled blood to the carotid artery to provide a temperature differential between the core body temperature and brain temperature.

Preferably the method comprises diverting blood flow returning from the brain to the body through the jugular vein through a second extracorporeal bypass, and warming or cooling said blood flow to a desired target temperature for maintaining said a desired core body temperature below the neck.

For example, the body is heated to a state of hyperthermia below the neck and the carotid blood flow to the brain is cooled. In a preferred embodiment, the method comprises maintaining a state of hyperthermia below the neck at a target core body temperature and cooling the carotid blood flow to the brain to maintain a near normal brain temperature, allowing the core body temperature to be raised above that typically possible during whole body hyperthermia, e.g. above 42° C.

The method has applications to treating a disease such as a form of cancer; HIV or AIDS related infection, a heat sensitive viral or bacterial infection, and may comprise administering chemotherapy while the body is in a state of hyperthermia.
If required, localized cooling of one or more of the lungs, spinal cord, testicles and other heat sensitive body parts and tissues, may be provided.

Yet another aspect of the invention provides a system for hyperthermic treatment characterized by:
means for extracorporeally cooling blood flowing from the body to the brain via at least one carotid artery,
and optionally, means for extracorporeally heating blood returning from the brain to the body via at least one jugular vein,
means for controlling the temperatures of the carotid blood flow to the brain for maintaining the brain at a desired temperature while maintaining a hyperthermic core body temperature from the neck down.

Another further aspect of the invention provides a system for extracorporeal blood treatment characterized by:
an arterial blood flow bypass circuit having input means for receiving arterial blood flow from the body and output means for coupling to a carotid arterial blood flow to the brain; heat exchange means for regulating a temperature of said carotid bypass blood flow to the brain;
pump means for controlling a flow rate and pressure of said carotid blood flow to the brain;
sensor means for monitoring temperature, flow rate and pressure of input and output blood flows, and
control means for controlling temperature, flow and pressure of the output carotid blood flow to the brain.

Preferably, the system is further characterized by:
a venous blood flow bypass circuit having input means for receiving venous blood flow from the brain, and output means for coupling to venous blood flow to the body, heat exchange means for regulating a temperature of said venous blood flow to the body; and
wherein said control means further provides for controlling temperature of the output venous blood flow to the body.

The control means is operable for establishing and maintaining a neck down body temperature differential with respect to a brain temperature, e.g. neck down hyperthermia relative to a normal brain temperature, for a predetermined treatment time. The temperature differential may be programmably modulated during a treatment duration.

Sensor means may be provided for receiving data indicative of a core body temperature and a cerebral core temperature, and wherein the control means maintains said required temperature differential between said input arterial blood flow and output carotid blood flow to provide a desired temperature differential between said core body temperature and said cerebral core temperature.

The venous bypass circuit comprises a similar pump and sensors for monitoring and control of the temperature, pressure and flow of blood returning to the body from the brain, i.e. via the internal jugular vein.

A yet further aspect of the invention provides an apparatus for extracorporeal blood treatment for thermotherapy comprising a cooling unit characterized by:
an arterial blood flow bypass circuit having an input for receiving arterial blood flow from the body and an output for delivering arterial blood flow to the brain;
a pump for pumping blood through the bypass circuit;
a refrigeration unit and heat exchange means for cooling the blood flow through the bypass circuit;
temperature sensors for monitoring temperatures of input and output blood flows;
pressure sensors for monitoring pressures of input and output blood flows;
control means for monitoring temperature, pressure and flow parameters and regulating temperature, pressure and flow at the output for delivering arterial blood flow to the brain at a temperature cooler than the input arterial blood flow from the body.

The apparatus may further comprise a corresponding heating unit for heating blood returning from the brain to the body, or the apparatus may comprise another cooling unit for regulating the temperature of blood from the brain to the heart and lungs.

Apparatus may alternatively comprise an arterial or venous blood flow bypass circuit having a heat exchanger comprising both heating and cooling elements to enable regulation of the temperature of output blood flow to a desired higher or lower temperature relative to the input blood temperature.

During elevated hyperthermia with a higher core body temperature, e.g. >44° C. it may be beneficial to cool a portion of the venous blood returning to the heart such that the heart and lungs are exposed to a venous blood at a temperature which is slightly lower than the below neck core body temperature. This may allow the majority of the body from the neck downwards to be exposed to more elevated temperature while keeping the heart and the blood flowing to the lungs at a slightly lower temperature thereby delaying the onset adverse reactions, such as cardiac arrest.

Thus methods, systems and apparatus according to aspects of the invention allow for a below neck core body temperature to be raised and maintained at an elevated temperature while the brain is kept at a lower temperature, or preferably, near normal temperature, thereby allowing the maximum attainable hyperthermic treatment temperatures to be increased, or alternatively, for the treatment duration to be extended. By maintaining the brain at a temperature differential from the body, to reduce risk of brain damage, as well as the physiological response, which is induced by the hypothalamus, a major limitation to raising the body temperature above 42° C. is overcome. Thus, for example, forms of cancer which are situated below the neck could be treated more aggressively using hyperthermia, while the brain would be maintained at relatively normal core body temperatures, or closer to a normal core body temperature.

Thus, systems, apparatus and method according to embodiments of the invention may provide for significantly extending the maximum treatment temperature, or alternatively the treatment duration, to which a patient can be safely subjected while reducing risk of serious side effects. Beneficially, if core body temperatures greater than 42° C. could be maintained for a reasonable treatment duration without adversely affecting the patient, hyperthermia may be used to more effectively treat and potentially cure such diseases as cancer, HIV, Hepatitis C and potentially other diseases. Alternatively, treatment may be more effective if core body temperatures currently achievable, e.g. below 42° C., could be maintained for longer periods of time.

More particularly, the method provides for inducing hyperthermia from the neck down for the treatment of cancer or infections or chronic conditions listed previously. The body core temperature can be increased using extra-corporeal heaters of the blood, water blankets, RF, Infra-Red radiation, an incubator or any other heating mechanism.

Preferably, the method comprises maintaining the brain at a lower or normal temperature by sending the blood which travels through the carotid artery through an external heat exchanger, i.e. a thermal cooling system. This can be accomplished by using an extra-corporeal pump to draw blood from the carotid artery, send it through a cooling apparatus where it can be regulated to a near normal body temperature, e.g. 37° C., and re-inserting it in the carotid artery at a second entry point closer to the brain. Alternatively, arterial blood can be drawn from an artery in the arm or leg, for example, cooled down to a normal temperature using an extracorporeal cooling system, and reinjected into the carotid artery such that blood which is lower than the hyperthermic treatment temperature is flowing to the brain.

Given that the blood flowing to the brain is at a lower temperature than the desired below neck therapeutic temperature, in some embodiments, the blood which returns from the brain towards the heart in the jugular vein is preferably heated back to the target below neck core temperature. The heating can be accomplished by sending the blood through a second extra-corporeal bypass and heating it to the target temperature. The bypass may comprise using an extra-corporeal pump to draw the blood from the internal jugular vein, sending the blood to a heating apparatus to bring it to the target below neck core temperature, and reinserting it into the internal jugular vein at second location below the first location. Alternatively, blood can be drawn from the jugular vein, reheated to a desired temperature, and re-injected into a vein which is accessible in the arm or leg.

Although the extra-corporal heating system which is installed on the jugular vein should be sufficient to heat the patient to a target below neck core temperature, additional heating can be supplied using hot water blankets, inductive blankets or an incubator as is typically used to induce whole body hyperthermia, or another extra-corporeal heating device which can warm the blood and re-inject it into a vein thereby causing the body to warm up to a target temperature, or heating the body using electromagnetic waves such as infrared or radio waves.

Given that the brain is being maintained at a lower or normal temperature, the neck down body temperature can be increased above the 42° C. typically used for Whole Body Hyperthermia or alternatively the treatment duration can be extended.

Thus improved systems, apparatus and methods are provided for extracorporeal blood processing for establishing and maintaining below the neck body temperature differential, i.e. hypothermia or hypothermia, for thermotherapy while maintaining the brain at a relatively normal temperature. In particular, hyperthermia treatments may be provided at higher temperatures, e.g. 42° C. or more and/or with extended duration, with reduced risk of brain damage and other detrimental effects, for treatment of cancer and other diseases and medical conditions.

The foregoing and other objects, features, aspects and advantages of the present invention will become more apparent from the following detailed description, taken in conjunction with the accompanying drawings, of preferred embodiments of the invention, which description is by way of example only.

BRIEF DESCRIPTION OF THE DRAWINGS

FIG. 1 is a schematic of the key arteries of the neck and brain and how they branch;

FIG. 2 is a pictorial of the Circle of Willis to highlight how cool arterial blood can be made to flow from the internal carotid artery to parts of the brain which are normally supplied by the vertebral-basilar arteries;

FIG. 3 is a high level diagram showing a system according to a first embodiment of the invention, showing how bypass circuits comprising Cooling Units and Heating Units are attached to the patient when all the catheters are inserted into arteries or veins of the neck;

FIG. 4 is a high level diagram showing a system according to a second embodiment showing how bypass circuits comprising the Cooling Units and Heating Units are attached to the patient when one catheter is inserted into an artery or vein of the neck and the other catheter for the same circuit is inserted into an artery or vein of the arm;

FIG. 5 is a schematic diagram showing the key parts of an apparatus according to a first embodiment comprising an Extra-Corporeal Cooling Unit;

FIG. 6 is a schematic diagram showing the key parts of an apparatus according to a first embodiment comprising the Extra-Corporeal Heating Unit;

FIG. 7 shows the temperature profile of key parameters during implementation of a method according to a first preferred embodiment of the invention. The diagram shows the temperature of the brain (cerebral temperature), temperature of blood flowing through the jugular vein after passing through the extra-corporeal heating unit and the patient's core body temperature;

FIG. 8 shows the key heat transfer parameters during implementation of a method according to the first preferred embodiment of the invention (same implementation as FIG. 7). The diagram shows heat added to the blood flowing through the internal jugular vein by the extra-corporeal heating unit, heat removed from the arterial blood flowing up the carotid artery by the extra-corporeal cooling unit, and heat loss to the surrounding environment;

FIG. 9 shows the temperature profile of key parameters during implementation of a method according to a second preferred embodiment of the invention. The diagram shows the temperature of the brain (cerebral temperature), temperature of blood flowing through the jugular vein after passing through the extra-corporeal heating unit, the patients core body temperature and the temperature of the arterial blood flowing up the internal carotid after passing through the extra-corporeal cooling unit. In this embodiment the arterial blood is cooled below 37° C. in order to keep the brain temperature as a relatively constant temperature;

FIG. 10 shows the key heat transfer parameters during implementation of a method according to the second preferred embodiment of the invention. The diagram shows heat added to the blood flowing through the internal jugular vein by the extra-corporeal heating unit, heat removed from the arterial blood flowing up the carotid artery by the extra-corporeal cooling unit, and heat loss to the surrounding environment;

FIG. 11 shows the temperature profile of key parameters during the implementation of a method according to a third preferred embodiment of the invention. The diagram shows the temperature of the brain (cerebral temperature), temperature of blood flowing through the jugular vein after passing through the extra-corporeal heating unit, the patients core body temperature and the temperature of the arterial blood flowing up the internal carotid after passing through the extra-corporeal cooling unit. The arterial blood is cooled below 37° C. to have an enhanced cooling effect on the brain. A two stage temperature profile is used to leverage step-down sensitization;

FIG. 12 shows the key heat transfer parameters during implementation of a method according to the third preferred embodiment of the invention. The diagram shows heat added to the blood flowing through the internal jugular vein by the extra-corporeal heating unit, heat removed from the arterial blood flowing up the carotid artery by the extra-corporeal cooling unit, heat loss to the surrounding environment and heat added to the patient by Infra Red Heating Lamps;

FIG. 13 shows the temperature profile of key parameters during implementation of a method according to the fourth preferred embodiment of the invention. The diagram shows the temperature of the brain (cerebral temperature), temperature of blood flowing through the jugular vein after passing through the extra-corporeal heating unit, the patients core body temperature and the temperature of the arterial blood flowing up the internal carotid after passing through the extra-corporeal cooling unit. The arterial blood is cooled below 37° C. to have an enhanced cooling effect on the brain. Furthermore, the brain is cooled to a temperature below its normal temperature;

FIG. 14 shows the key heat transfer parameters during implementation of a method according to the fourth preferred embodiment of the invention. The diagram shows heat added to the blood flowing through the internal jugular vein by the extra-corporeal heating unit, heat removed from the arterial blood flowing up the carotid artery by the extra-corporeal cooling unit, heat loss to the surrounding environment and heat added to the patient by Infra Red Heating Lamps;

FIG. 15 shows the temperature profile of key parameters during the implementation of a method according to a fifth preferred embodiment of the invention. The diagram shows the temperature of the brain (cerebral temperature), the patients core body temperature and the temperature of the arterial blood flowing up the internal carotid after passing through the extra-corporeal cooling unit. In this embodiment, blood flowing down the internal jugular vein is not passed through the Extra-Corporeal heating unit and as such this blood flow tracks the cerebral temperature with a delta of −0.3° C.;

FIG. 16 shows the key heat transfer parameters during implementation of a method according to the fifth preferred embodiment of the invention. The diagram shows heat removed from the arterial blood flowing up the carotid artery by the extra-corporeal cooling unit, heat loss to the surrounding environment and heat added to the patient by the warm water bath;

FIG. 17 shows the temperature profile of key parameters during the implementation of a method according to a sixth preferred embodiment of the invention. The diagram shows the temperature of the brain (cerebral temperature), the patients core body temperature and the temperature of the arterial blood flowing up the internal carotid after passing through the extra-corporeal cooling unit. In this embodiment, blood flowing down the internal jugular vein is cooled to a relatively low temperature of 30° C. Cooling the venous blood helps preferentially cool the heart and lungs to allow more aggressive therapeutic temperatures to be maintained while protecting these key organs;

FIG. 18 shows the key heat transfer parameters during implementation of a method according to the sixth preferred embodiment of the invention. The diagram shows heat removed from the arterial blood flowing up the carotid artery by the extra-corporeal cooling unit, heat loss to the surrounding environment and heat added to the patient by the warm water bath. Large amounts of heat are removed by the Extra-Corporeal heating unit the Internal Jugular vein since this blood is being cooled to 30° C.;

FIG. 19 shows a schematic cross section of the Internal Carotid artery and two 16 gauge catheters which have been inserted into this artery to implement the extra-corporeal circuit;

FIG. 20 shows the pressure on the Intake Line and Outlet Line necessary to draw a certain flow rate through the 16 gauge catheters, assuming an arterial pressure of 100 mmHg;

FIG. 21 shows the arterial pressure on the upstream side of the outlet catheters (P_cerebral) and the intrinsic arterial pressure (P_arterial) as a function of the volumetric blood flow being pumped through the extra-corporeal by-pass circuit;

FIG. 22 shows the volumetric blood flow being supplied to the brain by the internal carotid, as a function of the blood flow through the by-pass circuit. It also shows a sudden inflection point in the temperature of the arterial blood entering the Intake Line of the Cooling Unit, as the direction of the arterial blood flowing between the two catheters reverses; and FIG. 23 shows a cross section of the heat transfer block.

DETAILED DESCRIPTION OF PREFERRED EMBODIMENTS

Systems, apparatus and methods according to preferred embodiments of the present invention provide for thermally regulating the head or brain independently from the rest of the body in such a way that the below neck core temperature can be increased sufficiently to treat a targeted disease, while maintaining the brain at a temperature which is near the normal human core temperature of approximately 37° C. or at least at a temperature which is lower than the hyperthermic treatment temperature to which the body is being exposed from the neck down.

As will be described in detail below with reference to FIGS. 3, 4 5 and 6, systems and apparatus according to embodiments of the invention provide for inducing Hyperthermia from the Neck Down, for example, for the treatment of cancer or other infections conditions.

Hyperthermia from the Neck Down is accomplished by the following method. The body core temperature can be increased using extra-corporeal heaters of the blood, water blankets, an incubator, RF radiation or infrared radiation or any other heating mechanism. Given that the brain is primarily cooled by cerebral flood flow, the brain can be maintained at a lower temperature than the core body temperature by sending the blood which travels through the internal carotid artery through an external thermal cooling system. This is accomplished by using an extra-corporeal pump to draw blood from the carotid artery, send it through a cooling apparatus where it can be regulated to 37° C. or at a temperature which is lower than the below neck hyperthermic treatment temperature, and re-inserting it in the carotid artery at a point above where is was withdrawn. The vascular clamp or any other device which can either totally or partially restrict blood from flowing directly up the carotid can be used, but it is not essential. Alternatively, blood can be withdrawn from an artery in a location which is easily accessible such as a leg or arm using an extracorporeal pump, sent through a cooling system, and reinjected into the carotid artery. This will ensure that the arterial blood supply to the brain is at a lower temperature than the core body temperature from the neck down.

Before describing the method, and system and apparatus of the embodiments in detail, it will be helpful to explain key concepts of thermal regulation of the body, and to introduce terminology relating to the circulatory system of the head and neck, with reference to FIGS. 1 and 2.

Thermal Regulation of the Body.

If one considers the human body with careful attention to heat generation and heat transfer we can understand why the brain is the first element to be damaged by an elevated core body temperature. Firstly, an alert adult human dissipates approximately 20% of his total energy in the brain while the brain accounts for a mere 2% of the total body mass. Under resting conditions, neurons require several orders of magnitude more energy than other cells. The power consumption of a single central neuron is about 0.5-4.0 nW, 300-2500 times more than the average body cell (1.6 pW). Since all energy used for neural metabolism is finally transformed into heat, neural activity should be accompanied by heat release. This metabolic heat continuously dissipates from brain tissue. If we further consider that the brain is encased in the cranium and that the dissipated heat per unit mass is ~10× greater than the total body average, there seems to be very little opportunity for cooling the brain other than through cervical blood flow. Therefore, brain circulation appears to be the primary means of heat removal from the brain to the lungs and skin, and then to the external environment. E. Kiyathin provides a very good overview of brain hyperthermia during physiological and pathological conditions [11] as well as in vivo measurements of arterial blood temperature going to the brain and venous blood temperature returning from the brain.

If we assume that the majority of the heat dissipated by the brain is dissipated by cerebral circulation, and then apply a basic conservation of energy relation, we will expect that the veinous blood leaving the brain through the internal jugular vein, would be at a higher temperature than blood entering the brain via either the internal carotid or vertebral arteries. This principle can be expressed by the following equation:

$$\dot{Q}_{brain} = \dot{V} \cdot \rho \cdot c_p (T_{jugular} - T_{arterial})$$

Where:
$\dot{Q}_{brain}$ is the heat dissipated by the brain in Watts.
$\dot{V}$ is the cervical blood flow to the brain in ml/sec.
$\rho$ is the density of blood in grams/ml.
$c_p$ is the specific heat of blood in J/g° C.
$T_{jugular}$ is the temperature of the venous blood leaving the brain through the internal jugular in ° C.
$T_{arterial}$ is the temperature of the arterial blood entering the brain through the internal carotid or basilar arteries.

In a steady state condition where the brain is at equilibrium and the heat being produced by the brain is being transferred to and carried away by the cervical blood flow, the equality will hold true. If we apply values typical for an adult male to the above relation, and assume a cardiac output of 5 liters/minute, with the cervical portion accounting for 20% of the cardiac output (16.6 ml/sec), the blood density to be $\rho=1.06$ g/ml and assume the specific heat for blood to be $c_p=3.77$ J/g° C., we find that the differential temperature between the arterial supply and veinous outflow is approximately 0.3° C. A 0.3° C. temperature differential between the arterial and venous blood was measured in humans in [11] and agrees with our calculation. Given that the brain is generating heat and that its primary mode of cooling is by transferring heat to the cerebral blood, the temperature of the brain will be inherently higher than that of the venous blood, and the venous blood will be at a higher temperature than the arterial blood. The arterial blood is approximately at the core body temperature.

Furthermore, researchers have observed and reported an intra-brain temperature gradient. Temperatures recorded from more dorsally located structures of the brain such as the hippocampus were up to 1° C. lower than ventrally located structures (i.e., ventral striatum, ventral tegmentum and hypothalamus). More centrally located portions of the brain such as the thalamus and dorsal striatum had intermediate values. Direct measurements of arterial blood temperature have shown that it is always cooler than any brain structure. This implies that the ventrally located structures of the brain are up to 1° C. above the arterial blood temperature or core body temperature. The hypothalamus, which regulates body temperature, is located in the ventral portion of the human brain and as such is subjected to the highest temperatures and is therefore well situated to act as the temperature set point for the human body. The higher temperatures associated with the more ventrally located portions of the brain have been partly attributed to the fact that this area of the brain is constantly active and as such dissipates more energy. Given that the brain temperature is higher than the core body temperature, when the core body temperature starts to rise as a result of hyperthermia or heat stroke or an illness, the brain is generally the first element which begins to suffer irreversible damage. As such, a system which can increase the core body temperature from the neck down, while maintaining the head or brain at a lower or normal temperature, will extend the achievable treatment temperatures or treatment durations.

The sympathetic nervous system attempts to maintain all parts of the body at a desired temperature. The central temperature set point is in the hypothalamus, in the ventral portion of the brain. Temperature stability is maintained by the hypothalamus via a variety of feedback mechanisms. The temperature setpoint to which the hypothalamus regulates the body exhibits a circadian rhythm and is reset occasionally to a higher level by infectious agents and endotoxins. During therapeutic induction of hyperthermia however, the hypothalamus will attempt to maintain the body at its intended setpoint. During the initiation of hyperthermia, the sympathetic nervous system will respond by attempting to counteract the increasing temperature. The blood vessels will dilate, the heart rate rises and blood flow increases in an attempt to carry heat to the surface of the body where it can be dissipated to the environment. On average the heart rate increases 11.7 beats per minute per ° C. of increased temperature. For an adult with a typical heart rate of 70 beats per minute at 37° C., the heart rate would increase to 105 beats per minute at 40° C. and 140 beats per minute at 43° C. Systolic blood pressure increases to drive the blood flow but diastolic pressure decreases due to the decreased blood resistance of the dilated blood vessels and decreased blood viscosity at elevated temperatures. Given the increased heart rate and blood pressure, hyperthermia is currently contraindicated for most patients with cardiac conditions. Respiration rates also increase and breathing becomes shallower. The body also attempts to cool itself through perspiration, which results in dehydration and weight loss despite fluid intake. At ~42.5° C., thermocompensatory mechanisms cease to function and the body displays symptoms of advanced heat stroke, specifically, lack of sweating, rapid heart beat, Cheyne-Stokes breathing, central nervous system dysfunction and loss of consciousness. Breathing ceases despite the continuation of a heart beat. The adverse effects of hyperthermia listed above can be alleviated by the proposed system since the hypothalamus remains at a lower or normal temperature and is not directly aware that the core body temperature from the neck down is being increased above the desired setpoint. This allows a patient to be subjected to hyperthermic treatment for longer periods of time.

Thus, systems, apparatus and methods according to embodiments of the invention seek to provide two benefits. The first is that the core body temperature from the neck down can be increased to a desired therapeutic level while the brain is maintained at a lower or relatively normal temperature thereby reducing adverse effects to the brain which would normally be caused by an elevated core body temperature. The second benefit arises since the hypothalamus, which controls thermoregulatory compensation mechanisms of the sympathetic nervous system, is maintained at a near normal temperature, and is thus not directly aware that the temperature from the neck down is being increased above the setpoint, and as such the thermoregulatory compensation mechanisms are suppressed.

Circulatory System of the Head and Neck.

Before proceeding to a detailed description of embodiments of the invention, it is important to understand the circulatory system of the head and neck. There are two sets of arteries which carry blood up through the neck to supply the blood to the brain. The left and right internal carotid arteries supply the majority of the blood to the brain while a smaller quantity is supplied by the left and right vertebral artery. The carotid arteries carry approximately 4 times more blood than the vertebral arteries. Similarly, the majority of blood returning from the brain, down through the neck, flows through two sets of veins, primarily the internal jugular vein and the vertebral vein. The majority of the blood is carried by the internal jugular while a smaller quantity is carried by the vertebral veins. Given that the internal carotid arteries and jugular veins are superficially located near the surface of the neck and they carry approximately 80% of the blood to and from the brain, they are ideal for implementing the extracorporeal bypass circuit to thermally regulate brain temperature at a lower setpoint that the core body temperature from the neck down.

FIG. 1 is a schematic of the arterial system of the head and neck which shows some of the arteries which are of interest to this discussion. It is by no means complete but rather is a diagram which shows the logical interconnection and branches of the internal carotid and vertebral arteries along with some of their major branches. The arterial system commences with the pulmonary artery, which carries oxygen depleted blood from the right ventricle, to the lungs where the gas transfer occurs, and back to the left ventricle. The left ventricle then pumps the oxygenated blood into the aorta. Some of the major branches from the aorta, which ultimately carry blood up to the head and neck, are the innomate which leads to the right sub-clavian artery, the left subclavian and the left common carotid artery. Branching off the right subclavian we have the right common carotid and right vertebral arteries. The origin of the left and right carotids differ. The right common carotid originates from the subclavian artery whereas the left common carotid originates directly from the aorta arch. From the left subclavian comes the left vertebral artery.

The carotid arteries divide into the external carotid and internal carotid. The external carotid and its branches supply blood to portions of the head and neck but those portions which are supplied are not internal to the skull and as such not key to regulating brain temperature. The internal carotid, once it branches off from the main carotid, travels directly up the neck and enters the skull through the carotid canal. Once within the skull the internal carotid and its branches supply blood to the brain. The major branches of the internal carotid are shown in the diagram. They are the ophthalmic artery, anterior choroidal artery, anterior cerebral artery, middle cerebral artery and posterior communicating artery. Since the internal carotid is part of the cooling bypass circuit, the blood flowing through the internal carotid, and all of its branches, would be regulated to a lower temperature than the hyperthermic treatment temperature to which the body is being exposed from the neck down.

Major branches of the internal carotid and which portions of the brain they supply The anterior cerebral arteries are a pair of arteries that supply oxygen to most medial portions of the frontal lobes and superior medial parietal lobes. These two arteries are part of the Circle of Willis, which will be discussed further down.

The middle cerebral artery is one of the three major paired arteries that supply blood to the cerebrum. It arises from the internal carotid and continues into the lateral sulcus where it branches and supplies many parts of the lateral cerebral cortex. It also supplies blood to the anterior temporal lobes and the insular cortices.

The posterior communicating artery is one of a pair of right-sided and left sided blood vessels in the circle of Willis. It connects the three cerebral arteries of the same side. Anteriorly, it is one portion of the terminal trifurcation of the internal carotid artery. The anterior cerebral artery and the middle cerebral artery are the other two branches of the trifurcation. Posteriorly, it communicates with the posterior cerebral artery.

The ophthalmic artery is a branch of the internal carotid artery, which supplies branches to the eye and other structures in the orbit. It enters the orbit through the optic canal, together with the optic nerve.

The anterior choroidal artery is a fairly small artery, which branches off the internal carotid. This artery supplies the choroid plexus, optic chiasm, internal capsule, lateral geniculate body, globus pallidus, tail of the caudate nucleus, hippocampus, amygdale, substantia nigra, red nucleus and the crus cerebri.

The vertebral arteries progress upwards through the neck and give rise to the spinal and muscular arteries. Once the vertebral arteries enter the skull, there are multiple branches which provide blood to the brain and spinal cord. Specifically the posterior inferior cerebella, medullary, anterior spinal, posterior spinal and meningeal arteries. The left and right vertebral arteries join at the base of the skull to form the basilar artery. From the basilar artery branch the multiple small arteries collectively referred to as the pons, the anterior inferior cerebellar and the posterior cerebral arteries.

Areas of the brain are supplied by the vertebral arteries and their branches

The meningeal branches of the vertebral artery supplies the falx cerebella.

The posterior spinal artery branches from the vertebral artery and ultimately enters the sub arachnoid cavity to supply the spinal cord with oxygenated blood.

The anterior spinal artery supplies the anterior portion of the spinal cord.

The posterior inferior cerebellar artery is the largest branch of the vertebral, and is one of three main arterial blood supplies for the cerebellum. Branches of this artery supply the choroid plexus and fourth ventricle.

The basilar artery is formed when the left and right vertebral arteries join. The basilar artery supplies blood to the posterior part of the circle of Willis and amastomoses with blood supplied to the anterior part of the circle of Willis from the carotid arteries.

From the Basilar artery arise the anterior inferior cerebellar artery which supply the superior and inferior aspects of the cerebellum as well as the smaller pontine branches.

The basilar artery then divides into the Posterior cerebral artery and the Superior cerebellar artery.

The posterior cerebral artery is one of a pair of blood vessels that supplies oxygenated blood to the posterior aspect of the brain, the occipital lobe.

The superior cerebellar artery supplies the pineal body, the anterior medullary velum and the tela chorioidea of the third ventricle.

Given that the hypothalamus controls the thermoregulatory compensation mechanisms of the sympathetic nervous system it is important to consider which arterial system supplies this key area with oxygenated blood. The hypothalamus is a small almond size part of the brain and is co-sited with the pituitary gland. There are two arteries which supply the hypothalamus and pituitary gland with oxygenated blood. Specifically, they are the superior hypophysial artery and the inferior phyophysial artery. The superior hypophysial artery supplies the pars tuberalis, the infundibulum of the pituitary gland and the median eminence. It is a branch of the posterior communicating artery which branches from the internal carotid artery in the circle of Willis. The inferior hypophysial artery is an artery supplying the pituitary gland. It is a branch of the internal carotid artery. It is important to note that the two arteries which supply the hypothalamus with blood originate from the carotid as opposed to the vertebral arteries. As such, if we were only to thermally regulate the blood travelling through the carotid arteries, and allow warmer blood to travel through the vertebral arteries, we would nevertheless be sending cooler blood to the hypothalamus and would therefore minimize the thermoregulatory compensation mechanisms which would normally arise from an elevated core body temperature.

Circle of Willis

The final area of the cerebral vascular system that we need to discuss carefully is the Circle of Willis. The Circle of Willis connects the internal carotid and vertebral/basilar arterial systems together to provide a redundant or collateral circulation to the brain. As can be seen in FIG. 1 the left and right internal carotids branch to their respective anterior cerebral arteries. The two anterior cerebral arteries are connected by the anterior communicating artery. The anterior communicating artery therefore allows blood to flow from left to right or vice versa, to and from the areas supplied by each of the internal carotid arteries. Similarly, the basilar artery branches into the posterior cerebral arteries. The posterior cerebral arteries are then connected to the respective internal carotid arteries by the posterior communicating arteries. This allows blood to flow from front to back or vice versa, from areas typically supplied by either the vertebral/basilar arteries or the carotid arteries. A drawing of the Circle of Willis can be seen in FIG. 2.

Typically, under normal conditions the Circle of Willis will provide a redundant path in the event that one of the key arteries is either blocked or damaged. For example, if the vertebral arteries were blocked at the juncture of one of the vertebral arteries such that the basilar artery were no longer able to receive oxygenated blood, there would be a pressure drop in the basilar artery. As a result of the Circle of Willis, blood would begin to flow from the internal carotid arteries, through the Posterior Communicating arteries to feed the Posterior Cerebral arteries and the basilar artery.

In this application, given that the carotid arteries are fairly superficial (i.e. located close to the body surface) compared to the vertebral arteries, it is easier to implement the thermal bypass system on the carotid arteries. By increasing the vascular pressure on the internal carotid arteries, it is possible to induce the cooler, thermally adjusted blood to flow from the carotid arteries, through the Circle of Willis and supply those areas of the brain which would typically be supplied by the vertebral and basilar arteries. As such, although the bypass system which cools the arterial blood is only implemented on the carotid arteries, it would be possible to supply most of the brain with the cooler blood.

PREFERRED EMBODIMENTS

We will now describe two preferred implementations which differ primarily in the placement of catheters for coupling of one or more circulatory bypass circuits or loops of the system for extracorporeal blood treatment which provide for temperature regulation of arterial or venous blood flow. In the first implementation all catheters are connected to blood vessels in the area of the neck (see FIG. 3). In the second preferred implementation, one catheter is inserted into a blood vessel of the neck, while the second catheter of the same circuit is made to a less critical blood vessel such as in an arm, leg or torso (see FIG. 4).

First Preferred Embodiment of the Invention

A high level block diagram of one preferred embodiment of the invention can be seen in FIG. 3. This is a basic diagram which highlights the human body vascular system and shows how the Neck Down Hyperthermia System would be coupled to the human body via first and second circulatory bypass loops for extracorporeal blood circulation. Each by pass loop comprises heat exchangers including respective left and right cooling units 400 and 600 and left and right heating units 500 and 700. A control system 300 comprises a Computer Data Acquisition/Control Module 117, coupled to respective heating units 500 and 700 and cooling units 400, 600 via a Data Acquisition control bus 116, and also comprises a suitable user interface.

Access to the blood vessels can be gained by using the well known Seldinger technique, named after Dr. Sven-Ivar Seldinger, a Swedish radiologist. The desired blood vessel is punctured with a sharp hollow needle called a trocar, with ultrasound guidance if necessary. A round-tipped guidewire is then advanced through the lumen of the trocar, and the trocar is withdrawn. A sheath or catheter can be passed over the guidewire into the blood vessel. After passing the sheath or catheter the guidewire is withdrawn. The Seldinger technique is a common method of introducing an arterial catheter. Using this method, arterial catheters can be inserted into the carotid arteries in the neck, or for other embodiments into other arteries in the arm or leg, or torso as appropriate.

FIG. 3 shows how the Cooling and Heating Units are attached to the patient. In this setup, all arterial and venous catheters are connected to the neck. To keep the system as flexible and as redundant as possible, we are using a separate heating and cooling unit for each of the left and right sides.

Cooling Unit 400 cools the blood travelling up the right internal carotid. Blood is drawn out of the right internal carotid by a catheter which is attached to Inlet Line 401, where it is carried to Cooling Unit 400, and the temperature of the blood is cooled down to a target temperature of say 37° C., after which it is carried back to the patient by Outlet Line 402, where it is reinjected into the right internal carotid, at a point above where it was extracted. Similarly, Cooling Unit 600 cools the blood travelling up the left internal carotid. Blood is drawn out of the left internal carotid by a catheter which is attached to Inlet Line 601, where it is carried to Cooling Unit 600, and the temperature of the blood is cooled down to a target temperature of say 37° C., after which it is carried back to the patient by Outlet Line 602, where it is re-injected into the left internal carotid, at a point above where it was extracted.

Heating unit 500 warms the blood travelling down the right internal jugular vein back to the therapeutic hyperthermic temperature, before it is allowed to mix with other blood already at the core body temperature. Blood is extracted from the right internal jugular vein by a catheter which is connected to Inlet Line 501, after which it is carried to Heating Unit 500, where it is heated back to a desired temperature to achieve or maintain patient hyperthermia, after which it is carried back to the patient by Outlet Line 502, where it is reinjected into the internal jugular vein by a catheter at a location below where it was extracted.

Similarly, heating unit 700 warms the blood travelling down the right internal jugular vein back to the therapeutic hyperthermic temperature, before it is allowed to mix with other blood already at the core body temperature. Blood is extracted from the left internal jugular vein by a catheter which is connected to Inlet Line 701, after which it is carried to Heating Unit 700, where it is heated back to a desired temperature to achieve or maintain patient hyperthermia, after which it is carried back to the patient by Outlet Line 702, where it is reinjected into the internal jugular vein by a catheter at a location below where it was extracted.

FIG. 4 shows an alternative embodiment with a different setup where one catheter from each extracorporeal circuit is in the neck and the other catheter of the same circuit is inserted in an artery in an arm. The advantage of this setup is that the neck is less crowded, and damage is minimized to the critical blood vessels of the neck.

Warm arterial blood is extracted from an artery of the arm by a catheter, carried to Cooling Unit 400 by inlet line 401 where it is carried to Cooling Unit 400, and the temperature of the blood is cooled down to a target temperature of say 37° C., after which it is carried back to the patient by Outlet Line 402, where it is reinjected into the right internal carotid to allow the cooled arterial blood to travel to the brain and maintain its temperature near 37° C.

Similarly, Cooling Unit 600 cools the blood travelling up the left internal carotid. Warm blood is drawn out of an artery of the arm by a catheter which is attached to Inlet Line 601, where it is carried to Cooling Unit 600, and the temperature of the blood is cooled down to a target temperature of say 37° C., after which it is carried back to the patient by Outlet Line 602, where it is re-injected into the left internal carotid to allow the cooled arterial blood to travel to the brain.

Heating unit 500 warms the blood travelling down the right internal jugular vein back to the therapeutic hyperthermic temperature, before it is allowed to mix with other blood already at the core body temperature. Blood is extracted from the right internal jugular vein by a catheter which is connected to Inlet Line 501, after which it is carried to Heating Unit 500, where it is heated back to a desired temperature to achieve or maintain patient hyperthermia, after which it is carried back to the patient by Outlet Line 502, where it is reinjected into a vein of the arm.

Similarly, heating unit 700 warms the blood travelling down the right internal jugular vein back to the therapeutic hyperthermic temperature, before it is allowed to mix with other blood already at the core body temperature. Blood is extracted from the left internal jugular vein by a catheter which is connected to Inlet Line 701, after which it is carried to Heating Unit 700, where it is heated back to a desired temperature to achieve or maintain patient hyperthermia, after which it is carried back to the patient by Outlet Line 702, where it is reinjected into a vein of the arm.

FIG. 5 shows a detailed schematic of an Arterial Blood Cooling Unit 100, as used for the system of the first and second embodiments. The purpose of this unit is to cool the warm arterial blood to a temperature which is more tolerable for the brain, prior to re-injection of the arterial blood into the carotid artery. A catheter is installed onto an artery from which blood is to be withdrawn and the catheter is connected to Intake Line 101 using appropriately sized medical tubing. The Pump 104, creates a suction to draw blood through the catheter via intake line 101. The preferred pump is a peristaltic pump although other types of pumps could be used. On the inlet line, prior to the pump, we have a Temperature Sensor 113 and a Pressure Sensor 110. The purpose of these two sensors is to measure the inlet blood temperature and pressure. In cases where the Intake and Outlet catheters are connected to the same artery, a temperature reading of Temperature Sensor 113, which is below the core body temperature, can indicate re-circulation between the outlet and inlet catheters. An accurate reading of the pressure on the intake line is very important to ensure that the pressure drop across the catheter is not excessive, indicating potential blockage. A minimal amount of instrumentation is placed on the intake side of the pump 104 to minimize the pressure drop on the suction side of the pump. On the output of the pump 104 we have a Flow Meter 105, which is used to monitor volumetric blood flow and ensure adequate circulation through the apparatus. The next instrument is a Pressure Sensor 111, which is used to measure the pressure on the output side of the pump. Comparing the pressure readings between Pressure Sensor 110 and Pressure Sensor 111, provides a direct reading of the pressure increase across the Pump 104. The next element in the line is the Heat Transfer Block 103 (i.e. heat exchanger). The purpose of the heat transfer block is to transfer heat from the warm arterial blood to the Sterilized Water Bath 106. The Heat Transfer Block 103 is designed with two objectives. The first is that the blood exiting the block should be very nearly equal to the temperature of the Sterilized Water Bath 106. The secondary objective is to minimize the amount of blood which is trapped in the Heat Transfer Block since it is undesirable to trap a large quantify of blood in the apparatus. This is accomplished by passing the blood through a very wide, but narrow rectangular channel to maximize the heat transfer surface between the blood and the heat transfer block, while minimizing the volume of blood in the block. On the outside of the heat transfer block which is in contact with the Sterilized Water, the block contains many heat fins to transfer heat from the water to the metal block as efficiently as possible.

FIG. 23 depicts a cross section of a proposed heat block 117. The heat transfer block 117 comprises of two similar half portions, Left Clamshell 120 and Right Clamshell 121, which form a clam shell structure. On the outside of the clam shell structure are External Heat Fins 123 for improving the efficiency with which heat is transfer from the liquid bath 106 to the heating block 117. The two clam shell portions preferably define a substantially rectangular, narrow Internal Channel 122 through which the blood travels. The channel is designed to reduce the volume of blood which is captive within the heat exchange block, for a desired heat transfer efficiency. This is accomplished by designing the Internal Channel 122 such that the Width, W, is significantly larger than the thickness, T, such that the surface area suitable for heat transfer is large relative to the cross section of the channel. Furthermore, a small thickness T ensures that the majority of the blood in the internal channel is within close proximity to the heat transfer surface. Optionally, Internal Heat Fins 124 can be designed on the inside surface of the Internal Channel 122 to improve the heat transfer efficiency. A medical grade O-Ring Grove 125 is provided for making a tight seal between the two clam shells, and the two parts to be separated for cleaning. During operation a positive pressure is maintained within the Internal Channel 122 compared to the liquid bath 106 such that any potential leakage will result in a small amount of blood escaping the unit, rather than having potential contaminants leak into the extra-corporeal circuit.

Leakage of Water into the heating block is prevented by having a higher pressure in the blood circuit than that of the Sterilized Water. The temperature of the Sterilized Water Bath 106 is monitored by Temperature Sensor 115. The Refrigeration Unit 108 cools a refrigerant, which is circulated through the cooling coils 107 to maintain the Sterilized Water Bath 106 at a desired temperature. A motor and impeller 109 circulate the water to ensure an equal distribution of temperature throughout the bath. On the outlet side of the heat exchanger we have Pressure Sensor 112 and Temperature Sensor 114. Temperature Sensor 114 is important, since it provides the temperature of the arterial blood before it is re-injected into the carotid artery. Pressure Sensor 112 provides a direct measurement of the arterial blood pressure on the input side of the catheter and gives an indication of the pressure drop across the Outlet catheter. All the temperature sensors, pressure sensors, flow meter, pump, motor impeller and refrigeration unit are connected by a Data Acquisition/Control Bus 116 so that they can be monitored and controlled by a Computer Data Acquisition/Control Module 117.

The Computer Data Acquisition/Control Module 117 has several purposes. The primary purpose of the module 117 of the control system 300 is to provide monitoring and control of other elements of the system for regulation of key parameters such as temperatures, flow rates, and pressures throughout the system. Temperature readings of the various sensing points are used to control the Refrigeration Unit to ensure that the temperature of the Sterilized Water Bath is very tightly regulated, thereby ensuring a desired arterial blood temperature at the outlet 102 of the system. The flow rate through the peristaltic pump 104 is also controlled, to ensure the desired blood flows through the system. Given that the peristaltic pump is a positive displacement pump, the volumetric flow rate is proportional to the rotation speed of the pump. The flow meter 105 provides verification that pump is indeed providing the desired flow. The multiple pressure sensors are primarily for alarm purposes and to detect if we have blockage in the system. If the inlet pressure sensor 110 drops below a certain threshold, it is an indication the Intake catheter is causing to much pressure drop for the desired volume of blood flow. Dropping the pressure further could cause gas accumulation in the blood which is not desirable and hence an alarm would be raised to inform the medical team that the inlet, and the speed of the pump would be reduced to ensure that the pressure does not drop below a certain threshold. Similarly, the Pressure Sensor 112 on the outlet of the system monitors the necessary pressure to drive the desired blood flow back into the carotid artery through the catheter. If the pressure becomes excessively high, this could indicate blockage of the catheter and an alarm would be raised. If the Outlet pressure becomes excessive, the control module will reduce the speed of the pump to ensure that the desired threshold is not exceeded. Additional pressure sensors can be used to measure the arterial pressure in the carotid artery directly, and at a location above the Outlet Catheter since this is the pressure being presented to the brain. The pressure sensor can be a separate device which is interfaced to the Control Unit 117.

To provide very stable temperature regulation, it is desirable that the water bath have a sufficient thermal mass to ensure a relatively small rate of temperature change. A 20 liter bath requires 83.4 kJ to create a 1° C. temperature change. With such a bath, even if the heat transfer block were transferring 500 W to the water, after 1 minute the bath would only experience a 0.36° C. temperature change. Such thermal mass provides ample time for the proportional control module to adjust the output of the Refrigeration Unit 108 to very tightly regulate the temperature of the water bath. Furthermore, in the event that the Refrigeration unit were to fail, the medical staff have a few minutes to respond before excessively warm blood begins to flow to the patients brain.

A peristaltic pump 104 provides a number of advantages. Firstly, it is a positive displacement pump. This implies that the flow rate through the apparatus can be easily controlled since it is directly proportional to the rotation speed of the pump. Secondly, the pump is self charging and is able to draw blood into the inlet line, by creating a suction on this line. Thirdly, the blood does not come into contact with the mechanical parts of the pump, but is fully enclosed in a sterilized tube which can be easily replaced to sterilize the system between patients, which minimizes the risk of infection.

FIG. 6 depicts a detailed schematic of the Heating Unit 200. The Heating Unit 200 is very similar to the Cooling Unit 100 described in FIG. 5 above, with a few exceptions. On the intake side of the system, the Heating Unit 200 received cool venous blood travelling back from the brain, through the internal jugular vein. The venous blood is extracted from the internal jugular using a catheter, where it is carried to Intake Line 101 by medical tubing. The purpose of the Heating Unit is to warm the blood to a desired temperature to induce or maintain hyperthermia, after which is exits the system through Outlet Line 102 where it is re-inserted into a vein by a catheter. As opposed to having a refrigeration unit and cooling coils to cool the bath of sterilized water, the heating unit has a power supply, which sends electricity through a heating element to warm the sterilized water bath to the desired temperature. Other than these exceptions, the sensors and the control system are very similar to the Cooling Unit described above.

Fluid Mechanical Consideration of Implementing the Extracorporeal Arterial or Venous Bypass:

Let us now discuss how to implement the vascular bypass. There are several objectives which are desirable. Firstly, we wish to implement an extracorporeal bypass of the blood flowing in an artery or vein to regulate its temperature by passing it through either the heating unit or cooling unit. Secondly, we wish to minimize trauma to the vein or artery. Thirdly, it is desirable to minimize the pressure variations of the cerebral arterial system.

The Poiseuille Flow equation is well known to those with a background in Fluid Mechanics. This equation can be used to predict the rate of fluid flow, or pressure drop, through a circular tube or channel such as a catheter. The equation applies for Laminar Flow, and other relations need to be used when the flow becomes turbulent.

Poiseuille's Equation States:

$$h_{loss} = \frac{128 \cdot \mu \cdot L \cdot \dot{V}}{\pi \cdot D^4 \cdot \rho}$$

where
$h_{loss}$ is the pressure drop through the tube.
μ is the viscosity of blood
L is the length of the tube or catheter
$\dot{V}$ is the rate of blood flow through the tube or catheter.
π is the well know constant 3.14.
D is the internal diameter of the tube or catheter.
ρ is the density of blood.

The other important fluid mechanical parameter which should be discussed is the Reynolds number. The Reynolds number is a dimensionless number which gives a measure of the ratio of internal forces to viscous forces and consequently quantifies the relative importance of these two effects and is used to predict whether a fluid will flow in a laminar or turbulent fashion. It is well known to individuals with a background in fluid mechanics. For flow in circular pipes or tubes the Reynolds number is given by:

$$R_{ey} = \frac{\rho \cdot D \cdot v}{\mu}$$

where v is the mean velocity of the fluid in the tube or pipe and μ is the viscosity of blood. The other variables have all been defined above.

Typically, for fluid flow in pipes or tubes with a circular cross section, a $R_{ey}$ of 2300 is used as the threshold for predicting the start of turbulent flow. As mentioned above, the Poiseuille equation applies only to laminar flow, and hence will only be applicable where the $R_{ey}$ number is less than 2300. In circumstances where the flow is turbulent, an empirical equation needs to be used to calculate pressure drop through the catheter or tube, as opposed to the Poiseuille equation.

In our application, the typical rate of blood flow through the internal carotid or internal jugular vein is on the order of 400 ml/min. The viscosity of normal blood is about 3 times greater than water, but varies considerably as a function of temperature and an individual's constitution, especially the packed cell volume. In certain individuals, the viscosity can be as much as 10× that of water. For our calculations we will assume a typical value for blood viscosity of $\mu=3.26\times10^{-3}$ Pa*s.

For a flow rate of 400 ml/min, and a blood viscosity of $\mu=3.26\times10^{-3}$ Pa*s, a catheter with an internal diameter of 1.2 mm would have a $R_{ey}=2300$. Catheter sizes are measured in Gauge, where the gauge is equal to 1 inch/(Outer Diameter of the catheter). Typical venous or arterial catheters have sizes of 12, 14 and 16 gauge, which would have outer diameters of 2.11 mm, 1.81 mm, and 1.587 mm respectively. Typically, the inner diameter is about 0.3 mm less than the outer diameter and as such 12, 14 and 16 gauge catheters would have internal diameters of 1.81, 1.51 and 1.29 mm respectively. For these sizes of catheters, assuming the above flow rates and viscosity, the $R_{ey}$ number would be 1530, 1830 and 2140 respectively. So, even for a relatively small 16 gauge catheter, the flow would be laminar.

Two examples of types of medical tubing used for transferring blood are Delmed Y-Blood Solution Set with an internal diameter of 3.0 mm, and Fenwal Large Bore Tubing with an internal diameter of 3.66 mm. For the above flow rate and viscosity, the resultant Reynolds number would be 920 and 754 respectively, which is well below the onset of turbulent flow.

FIG. 19 depicts a diagram showing two catheters 301 and 302 inserted into the carotid artery 304. The purpose of the diagram is to allow us to provide a sample calculation of how the flow rate through the Cooling Unit 100, affects the arterial pressure in the carotid artery, as well as to evaluate the pressure at various points of interest. The first catheter 302, is used for drawing blood from the artery into the Intake Line 101, so that it could be fed to the Cooling Unit 100. The second catheter 301, is used for returning the cooled blood from the Cooling Unit 100, and re-inserting it in the carotid artery in order to supply the brain with blood which has been cooled to a lower temperature than the hyperthermic treatment temperature to which the patient is being exposed from the neck down.

Under normal conditions let us assume that the patient has normal arterial blood pressure with a Systolic pressure of 120 mmHg and a Diastolic pressure of 80 mmHg. Lets calculate the pressure with a flow rate through the Carotid of 400 ml/min as discussed above, and when we are drawing the full flow (400 ml/min) through the Cooling Unit 100. As such, for a 16 gauge catheter, 4 cm long, with an internal diameter of 1.29 mm we would expect to see a pressure drop through the catheter of 13.2 kPa due to viscous losses (Poiseuille Equation). In addition, as a result of the sudden contraction as the flow transitions from the carotid with a diameter of 3 mm, to the catheter with an internal diameter of 1.29 mm the flow seems to experience an additional 10.7 kPa of head loss. The head loss as a result of sudden discontinuities is typically calculated using empirical equations. The result is that in order to draw blood into a 16 gauge catheter at a rate of 400 ml/min, the pressure at the Intake Line 101, at the point where it meets the catheter, must be at approximately 24 kPa lower than the arterial pressure in the Carotid artery. This would result in a negative gauge pressure in the Intake Line of approximately −10.7 kPa (gauge) or 90.6 kPa (absolute), assuming that the average pressure in the artery is ~100 mmHg. An absolute pressure of 90.6 kPa is well above the vapour pressure of blood, and as such the system should have no difficulty maintaining this flow rate. As the core body temperature increases above 37° C., the viscosity of the blood would drop considerably which would make drawing blood through the catheter that much easier. It is important to consider the pressure on the Intake Line carefully, because when the pressure approaches the vapour pressure of blood, this represents a hard limit beyond which we cannot draw additional blood through the catheter, and preferably a larger catheter should be used on the intake side to reduce the pressure drop. For flow rates of 400 ml/min however a 16 gauge catheter is adequate using a positive displacement pump similar to the one we are using in our system. The medical tubing, which is used on for the Intake Line 101, should be sufficiently rigid so that it does not collapse as a result of the negative gauge pressure on this line.

Similarly, the pressure of the Outlet Line 102, should be considerably larger than the pressure in the Carotid artery in order to push the blood back through the catheter and into the artery. Since we are also using a 16 gauge catheter, we would again experience a pressure drop of 12.8 kPa due to viscous losses. Furthermore, as a result of the sharp discontinuity when the fluid flow transitions from a catheter with an internal diameter of 1.29 mm to the carotid artery with an internal diameter of 3 mm, the fluid experiences a head loss of 13.2 kPa. The end result is that the pressure in the Outlet Line 102, must be about 26 kPa above the arterial pressure of the carotid. Modest positive pressures in this range are not a major issue since most medical tubing is more than capable of withstanding this.

The analysis on the jugular vein would be very similar. Given that we are targeting identical flow rates on the jugular vein, and the pressure drops across the Intake and Outlet catheters would be very similar to what we have absorbed above. The one key difference is that the jugular vein has a considerably lower vascular pressure of ~10 mmHg (typical, depends if the patient is standing or lying down). As such, the gauge pressure on the intake line would be lower ~−22.6 kPa gauge, or 78.6 kPa absolute. So, assuming we use identical catheter sizes, and we are driving equal flows through the venous circuit as we are through the arterial circuit, we would reach the vapour pressure of the blood on the venous circuit first. As a result, in some instances it might be beneficial to use a slightly larger catheter on the venous intake.

Let us now look at a more dynamic system and evaluate how the cerebral arterial pressure changes as we vary and control the rate at which blood passes through the Arterial Cooling Unit 100. As discussed previously, since the Cooling Unit 100, and Heating Unit 200, use a positive displacement peristaltic pump, the flow rate through the by-pass circuits can be easily controlled since it is proportional to the rotation speed of the pumps. As such, we are able to draw increasing amount of blood through the bypass circuits by increase the rotation speed of the pumps, so long as we do not drop below the vapour pressure of the blood on the intake side of the system. Let us now analyze how the Arterial Pressure of the Carotid will vary as we send increasing amounts of blood through the by-pass circuit. FIGS. 20, 21 and 22 are the result of an experiment.

FIG. 20 shows the pressure on the Intake Line 101 and Outlet Line 102, as a function of the flow being driven through the Cooling Unit 100, or Heating Unit 200. In this analysis we assume the mean arterial pressure on the Carotid artery is 100 mmHg (gauge). Initially, with a By-pass flow of 0 ml/min, there is no pressure drop through the intake catheter and as a result the pressure on the intake line is equal to the arterial pressure of 100 mmHg (gauge). On the outlet line, since the two catheters which have been inserted into the Carotid, partially block blood flow, there is a pressure drop through the carotid as a result of the blood flow of approximately 320 ml/min and hence the pressure on the Inlet Line is identical to the mean arterial pressure and is 80.1 mmHg. As the flow through the by-pass system is increased to say 400 ml/min, there is a larger pressure drop across the catheters, and the pressure on the Intake Line 101 and Outlet Line 102 drops to −80 mmHg (gauge) and 280 mmHg (gauge) respectively. As the flow rate through the bypass circuit increases further to 600 ml/min, the pressure drop across the catheters increases yet again and the pressure on the Intake Line 101 and Outlet Line 102 now becomes −170 mmHg (gauge) and 380 mmHg (gauge) respectively.

FIG. 21 shows the mean arterial pressure, as well as the arterial pressure presented to the brain by the carotid artery after the by-pass flow has been re-inserted into the artery. The location corresponds to the top of FIG. 19, which has been labelled "Exit Condition". These pressures are shown as a function of the blood flow being driven through the Heating or Cooling Bypass circuit. Without the catheters inserted, the pressure drop across the carotid would be minimal and the P_cerebral would be very nearly equal to P_arterial. As a result of the insertion of the two catheters, the cross section of the carotid is partially reduced, and as a result there is a resultant pressure drop of ~20 mmHg cross the carotid, between the tips of the two catheters. The 20 mmHg of pressure drop applies when there is no flow through the by-pass circuit. Gradually, as the flow through the by-pass circuit is increased to 400 ml/min (original flow rate through the carotid for the patient) the pressure presented to the brain at the exit of the diagram returns to the original value of 100 mmHg. Finally, as the flow through the by-pass circuit increase beyond the original 400 ml/min, the pressure presented to the brain begins to increase beyond the original arterial pressure. By doing this, we are able to increase the arterial pressure on the internal carotid artery, compared to the vertebral/basilar artery, and force blood to flow through the Circle of Willis as was discussed earlier. When we are sending 600 ml/min through the by-pass system, the mean arterial pressure at the exit of the diagram, has increased to ~110 mmHg, compared to the original value of 100 mmHg. This represents a 10% increase in mean arterial pressure. The pressure could be increased beyond this level by either increasing the flow through the by-pass circuit even further, or by increasing the resistance to flow in the internal catheter, between the tips of the Intake Catheter and Outlet Catheter. This can be achieved by applying pressure on the internal carotid, or alternatively if a double velum catheter were used, the outer sleeve of the catheter could be partially inflated (as in a balloon catheter) to partially restrict blood flow further.

FIG. 22 depicts the volumetric blood flow supplied to the brain by the carotid artery, as well as the rate of blood flow which travels directly up the internal carotid, between the tips of the intake and outlet catheters. Initially, when the blood flow through the by-pass circuit is 0 ml/min, all of the cerebral blood supply must travel directly up the internal carotid, and the total blood flow delivered to the brain is 320 ml/min. Prior to the insertion of the catheters the blood flow to the brain through this artery was 400 ml/min. The reduction is due to the increased resistance introduced by the partial blockage of the artery by the catheters. As the rate of blood flow through the by-pass circuit, which is being re-injected into the artery by the Outlet Catheter increases, the amount of blood which flows directly up the artery begins to decrease. As the amount of blood flowing through the by-pass system reaches the original value of 400 ml/min, there is no longer any blood flowing directly up the internal carotid, between the tips of the two catheters. When such a condition has been achieved, we are now passing substantially all of the blood through the Heating or Cooling Unit and the thermal by-pass is working effectively. From the perspective of the brain we have returned to the original condition, prior to the insertion of the catheters. The mean arterial pressure is once again 100 mmHg, and the cerebral blood flow from this artery is once again 400 ml/min.

As we increase the amount of blood flowing through the by-pass beyond the 400 ml/min, we start to see reverse flow between the two catheters. Since the carotid is partially blocked by the catheters, when the flow begins to reverse, the pressure must increase on the Exit side 304 of FIG. 19 compared to the Entrance side 303 of FIG. 19, to drive the blood flow. Gradually, as the blood flow through the by-pass circuit is increased to 600 ml/min, the cerebral blood flow to the brain has increased to 440 ml/min. The increased blood flow is primarily being pushed through the Circle of Willis and supplying areas of the brain which would normally have been supplied by the Vertebral/Basilar arteries.

The point at which we start to see blood flowing in reverse, can be detected by a sudden change in the blood temperature on the Intake Line. For example, the arterial blood flowing into the Intake Line 101, would be at the hyperthermic core temperature of the patient of say 42° C., as long as there is no reverse flow. Once we begin to see reverse flow, the flow into the Intake Line 101 is a combination of warm arterial blood at the hyperthermic temperature which is flowing up the carotid artery and the blood which is flowing in reverse between the Outlet catheter and Intake catheter and which has already been cooled to say 37° C. As can be seen in FIG. 22, there is a very sudden knee in the Intake Temperature curve as the flow begins to reverse. Advantageously, this phenomenon can be leveraged in the control algorithms of the system.

Other Embodiments

Although specific embodiments are described in detail above, it will be appreciated that other arrangements may be used in variants of these embodiments to achieve a neck down temperature differential, e.g. hyperthermia, relative to the brain, or hypothermia of the brain.

In the embodiments described above cooling and heating bypass circuits are provided for both right and left carotid artery and jugular vein blood flow. Other arrangements of heat exchangers for heating and cooling in these bypass circuits may be used. Selective cooling of other parts of the body, e.g. heat sensitive tissues may also be desirable, as will now be described.

The above described embodiments of the invention advantageously comprise thermally regulating the head or brain independently from the rest of the body in such a way that the below neck core temperature can be increased sufficiently to treat the targeted disease, while maintaining the brain at a temperature which is near the normal human core temperature of approximately 37° C. or at least at a temperature which is lower than the hyperthermic treatment temperature to which the body is being exposed from the neck down. In inducing Hyperthermia from the Neck Down for the treatment of cancer or other infections conditions, the body core temperature can also be increased using one or more of extra-corporeal heaters of the blood, water blankets, an incubator, RF radiation or infrared radiation, a warm water bath, or any other heating mechanism.

For neck down hyperthermia, as described above, given that the brain is primarily cooled by cerebral flood flow, the brain can be maintained at a lower temperature than the core body temperature by sending the blood which travels through the internal carotid or common carotid artery through an external thermal cooling system. This can be accomplished by using an extra-corporeal pump to draw blood from the carotid artery, send it through a cooling apparatus where it can be regulated to 37° C. or at a temperature which is lower than the below neck hyperthermic treatment temperature, and re-inserting it in the carotid artery at a point above where is was withdrawn. The vascular clamp or a balloon catheter, application of pressure or any other device which can either totally or partially restrict blood from flowing directly up the carotid can be used, but it is not essential. Alternatively, blood can be withdrawn from an artery in a location which is easily accessible such as a leg or arm using an extracorporeal pump, sent through a cooling system, and reinjected into the carotid artery. This will ensure that the arterial blood supply to the brain is at a lower temperature than the core body temperature from the neck down.

If the vascular pressure in the carotid artery can be maintained at a slightly higher pressure than the vertebral artery, then cool blood will flow through the Circle of Willis, from the internal carotid to the basilar and vertebral arteries and their respective branches, thereby cooling the majority of the brain and keeping it at a temperature which is lower than the hyperthermic treatment temperature to which the body is being subjected from the neck down.

The blood which returns from the brain towards the heart in the jugular vein will be at a lower temperature than the below neck hyperthermic treatment temperature. As such, it must be heated or else the cool blood flowing down through the internal jugular will have a cooling effect on the core body temperature. If we are relying on the internal jugular extracorporeal heating system as the primary method of inducing hyperthermia, then the blood must be heated to a slightly higher temperature than the target hyperthermic temperature to compensate for heat loss. If other methods of heating are being used, then the blood need only be heated sufficiently to prevent an excessive cooling. The blood heating can be accomplished by withdrawing blood from the internal jugular vein using an extracorporeal pump and sending the blood to a heating system. The bypass loop would comprise of using an extra-corporeal pump to draw the blood from the jugular vein, sending the blood to a heating apparatus to bring it up to the target temperature, and reinserting it into the jugular vein below a vascular clamp. Alternatively, the blood can be withdrawn from the internal jugular vein using an extracorporeal pump, heated to the target temperature, and re-injected into one of the major veins in a more accessible location such as the arm of leg.

Although the extracorporeal heating system which is installed on the jugular vein should be sufficient to heat the patient to a target below neck core temperature, additional heating can be supplied, if required, by using for example, one or more of Hot water blankets, inductive blankets or an incubator as is typically used to induce whole body hyperthermia.

An extra-corporeal heating device which can warm the blood and re-inject it into a vein thereby causing the body to warm up to a target temperature.

Heating the body using electromagnetic waves such as infrared or radio waves.

Given that the brain is being maintained at a near normal temperature of ~37° C. or at a lower temperature, the neck down body temperature can be increased above the 42° C. typically used for Whole Body Hyperthermia. Temperatures of up to 45° C. or potentially higher could be maintained from the neck downwards, and these temperatures may be sufficient to effectively treat cancer and other infectious diseases such as HIV, chronic inflammatory conditions such as ulcerative colitis and Crohn's disease, rheumatic conditions, bronchial asthma, chronic and recurrent viral infections and even conditions requiring detoxification.

Furthermore, given that the brain is being maintained at relatively normal temperature, the hypothalamus would not be directly aware that the body is being exposed to elevated core body temperature from the neck down, and as such the thermoregulatory compensation mechanisms would be reduced.

Other Considerations

Given that the brain is being maintained at a relatively normal temperature, it is unclear what other mechanisms would limit the ability of the human body from being exposed to elevated below neck core temperatures. To the inventor's knowledge, in all other reported experiments the temperature of the brain was increased along with the rest of the body and as a result the brain caused a response such as an accelerated heart rate, accelerated breathing, sweating etc., as it attempts to keep the body from over heating. With the system and methods according to embodiments of this invention, the brain is being maintained at a normal temperature while the remainder of the body from the neck down, is being exposed to increased temperatures.

Ancillary Cooling of Other Tissues

Cellular damage of the tissue being exposed to the elevated temperatures is, however, a concern. The spine, lungs and testicles would be the next elements which would likely be damaged as the below neck core temperature were increased towards 45° C. and above. The damage to these organs might be reversible and they may regenerate themselves after a recovery period. Otherwise, they can be preferentially cooled and maintained at a lower temperature than the therapeutic "below neck core temperature."

Spinal Cord: The spine can be cooled below the desired below neck hyperthermic treatment temperature by clamping cold packs along the back, in direct contact with the backbone. Local hyperthermia experiments have shown that an applied temperature differential (hot or cold) at the skin surface can penetrate into the body by about 2 cm. In hyperthermia experiments, the heat source is typically at approximately 45° C.; a mere 8° C. above the normal core body temperature and the temperature gradient is shown to penetrate by about 2 cm. The ability to cool the spin should be slightly more favourable since a cold pack can be as low as 0° C. and which represents a temperature differential of >40° C. compared to the therapeutic hyperthermic treatment temperature.

Testicles: The testicles are another part of the human body which are sensitive to heat. Given their location, it should be fairly simple to keep the testicles at a temperature slightly lower than the below neck core hyperthermic treatment temperature. The Testicles can be placed in contact with a cold pack for the duration of the treatment or they could potentially be immersed in a cold liquid by attaching some form of bag around the scrotum.

Lungs: The cells in the lungs may also be sensitive to elevated temperatures. One potential means of preferentially cooling the lungs would be to have the patient breath cold air. Air temperatures well below freezing can be provided to the patient for breathing which should favourably cool the lungs compared to the rest of the body. The patient can be made to breath through a forced air delivery system where the air has been chilled to a desired temperature. Air temperatures as low as −20° C. or even −30° C. can be breathed for prolonged durations without adverse effects. At such temperatures the cold air should reach deep into the alveoli and prevent the blood/air barrier from breaking down.

The preferential cooling of the Lungs, Testicles and Spinal Cord would represent a source of heat loss for the rest of the body. As such, if a desired target hyperthermic treatment temperature is to be maintained from the neck down, additional heat would need to be added to the body to overcome this heat loss. The additional heat can be applied in one of several ways already discussed above.

Experimental Systems:

The following experiments depict six simulations of methods according to preferred embodiments of the proposed invention, to demonstrate how Below the Neck Hyperthermia systems may be used clinically to treat patients.

Experiment A is the simplest implementation of the and uses a Cooling Unit on each of the Internal Carotid arteries to cool the arterial blood traveling to the brain in conjunction with a Heating Unit on each of the Internal Jugular Veins to heat the venous blood returning to the trunk and to induce a state of hyperthermia from the neck down.

Experiment B is similar to A above, with the exception that the Cooling Units used to cool the arterial blood in the Internal Carotid, is controlled in such as way as to keep the Cerebral temperature at a constant temperature.

Experiment C uses Infra Red lighting as an additional heating system in order to generate a faster temperature ramp. Also, the patient is exposed to two temperature plateaus, the first being warmer than the second, in order to benefit from the step down sensitization. The IR lights and the Jugular Heating Units are used to heat the patient to a desired temperature. The Cooling Units used to cool the arterial blood flowing up the Internal Carotid is regulated by a control loop which seeks to maintain the cerebral temperature constant.

Experiment D is similar to experiment C above with one exception. The cerebral temperature is regulated to a value slightly lower than normal to cause the patient to feel slightly chilly despite the elevated core body temperatures.

Experiment E uses a warm water bath to rapidly heat the patient to a very elevated core body temperature of 46° C. Cooling Units are installed on the Internal Carotid Arteries to maintain the brain at a relatively cooler temperature. No heating units are installed on the Internal Jugular veins since the cooling effect of not having them is minimal compared to the rate of heat transfer induced by the warm water bath.

Experiment F is similar to Experiment E, with two exceptions. The first is that the Cerebral temperature is regulated to a lower temperature than normal to have a protective effect on the brain. Secondly, a Cooling Unit is installed on the Internal Jugular veins as opposed to a Heating Unit. The cooling unit significantly cools the venous blood returning to the heart, such that the heart and lungs experience a cooler temperature than compared to the very elevated hyperthermic temperature to which the majority of the body is being exposed A more detailed description of each experiment follows:

Experiment A:

This is the most simple setup where we are using the Arterial Cooling Unit to keep the arterial blood flowing up the internal carotid artery cool, while we are using the Heating Unit to warm the blood flowing down the internal jugular vein, up to a necessary temperature to heat the body from the neck down in order to induce hyperthermia, and achieve a therapeutic effect. The target therapeutic temperature is approximately 42° C.

System Setup:

The Arterial cooling units will be installed on both the left and right internal carotid arteries to maintain the brain at a relatively cooler temperature, compared to the hyperthermic temperature to which the patient will be exposed from the neck down.

Arterial pressure on the Internal Carotid arteries will be increase slightly above the patient's normal arterial pressure, to favour blood flow through the carotid arteries as opposed to the vertebral/basilar arteries.

In this case the blood flowing up the Internal Carotid will be regulated to be at a temperature of about 37° C.

The Heating Units were installed on the Internal Jugular veins.

The Heating Unit will warm the blood flowing down the Internal Jugular vein to be at about 43° C.

No additional heat sources will be used. The patient will be allowed to rise to a temperature where thermal equilibrium is achieved, and will remain at this therapeutic level for approximately 24 hours. After 24 hours, the blood flow through the Heating Units will be stopped, and the patient will be allowed to drop back down to a normal temperature. Throughout the cooling process, the cooling units will continue to regulate the arterial blood flowing up to the brain through the internal jugular to ensure that the patient remains comfortable.

The patients Core Body temperature will be monitored closely throughout. If the patient is well insulated it is possible for his basal metabolism to exceed his rate of heat loss to the environment, at which point his core temperature could rise above the 43° C. temperature of the venous blood being injected into his internal jugular. If the patients temperature rises above the target temperature, blankets should be removed from the patient to increase his rate of heat loss to the environment such that his core body temperature from the neck down drop back to the target temperature. Similarly, if the patient's core temperature remains below the target temperature, then his rate of heat loss to the environment should be decreased by adding insulation such as blankets.

Experimental Results and Discussion:

The temperature profiles of the patient are shown in FIG. 7. At t=0, the bypass circuits were installed on both the internal jugular and internal carotid arteries. Over a period of approximately 5 hours, the patients core temperature increased from 37° C. to approximately 41.7° C. and it finally reached equilibrium at 41.9° C. a few hours later, and this temperature was maintained for the duration of the treatment. The cerebral temperature increased slightly above the initial starting temperature of 37.6° C., to a maximum temperature of 38.1° C. The slight increase in temperature is a result of having warm arterial blood flowing up the vertebral arteries, although the majority of the arterial blood was indeed flowing up the internal carotid arteries and this blood was being regulated to 37° C., hence the brain's cooler temperature. In the future, blood flowing up the internal carotid could be regulated to a temperature slightly lower than 37° C., such that the overall temperature of the brain remains at a normal temperature, despite the warmer blood flowing up the vertebral arteries. Blood flowing down the internal jugular vein, which was being bypassed through the heating units, was regulated to 43° C. for the entire 24 hour period.

The temperature rise/fall of the patient can be modelled by applying the basic conservation of energy principle to the patient:

$$T_{Core} = Q_{total}/(m \cdot c_p)$$

Where:

$Q_{total}$=total heat content of the patients body with respect to a reference temperature.

m=mass of patient $c_p$=average specific heat of the patients body.

$$Q_{total} = \int \dot{Q}_{environment} dt + \int \dot{Q}_{Carotid} dt + \int \dot{Q}_{Jugular} dt + \int \dot{Q}_{BasalMetabolism} dt$$

Where the first term is the rate of heat absorption/loss to the environment, the second term is the rate of heat addition/removal from the Arterial Cooling Unit applied to the carotid arteries, the third term is the rate of heat addition/removal from the Heating Unit attached to the patients internal jugular vein, and the final term is the rate of heat generation from the patients own Basal Metabolism. All of these parameters are measured in Watts, and they are integrated over time to calculate an energy value in Joules. If the summation of these terms is positive, then the amount of heat increases over time and the patient will experience an increase in his/her core body temperature. Conversely, if the summation of the terms is negative, then the amount of heat will decrease over time and the core body temperature of the patient will gradually drop.

The amount of heat added or removed by the Heating Unit and Cooling Unit respectively can be approximated as follows:

$$\dot{Q}_{Jugular} = \dot{V} \cdot \rho_{blood} \cdot c_{p\_blood}(T_{jugular} - (T_{cerebral} - 0.3° C.))$$

$$\dot{Q}_{Carotid} = \dot{V} \cdot \rho_{blood} \cdot c_{p\_blood}(T_{Carotid} - T_{Core})$$

Where:

$\dot{V}$ is the amount of blood flowing through the apparatus in ml/sec.

$\rho_{blood}$ is the density of blood in grams/ml.

$c_{p\_blood}$ is the specific heat of blood in J/gK.

$T_{jugular}$ is the temperature to which the Heating Unit regulates the venous blood prior to re-injecting into the patients vein.

$T_{carotid}$ is the temperature to which the Cooling Unit regulates the arterial blood prior to re-injecting into the patients internal carotid artery.

$T_{cerebral} - 0.3° C.$ is the temperature of the venous blood returning from the brain, in the internal jugular prior to going through the heating unit. We approximate this temperature to be the Cerebral temperature $-0.3° C$.

$T_{Core}$ is the core body temperature of the patient from the neck down, i.e. effectively the hyperthermic treatment temperature. The blood flowing from the heart, up into the internal carotid artery is assumed to be at approximately the neck down core body temperature.

All of the heat transfer parameters associated with this experiment can be seen in FIG. 8. Positive numbers indicate that heat is being added to the patient while negative numbers indicate that heat is being removed from the patient. At t=0, heat is being added to the patient at a rate of over 400 W from the heating unit while no heat is being removed from the Carotid Cooling Unit. This makes sense since the Jugular Heating Unit would be receiving blood at a fairly normal temperature of approximately 37.3° C., and heating it up to 43° C. Conversely, the Carotid Cooling Unit would be receiving arterial blood at the current core body temperature of 37° C., which is the desired temperature and hence no heat removal occurred. Gradually, as the patients core body temperature increases, the Carotid Cooling Unit begins to remove heat from the blood stream. As equilibrium is achieved, the summation of all the heat additional and removal streams should equal zero.

Experiment B:

This experiment is identical to the previous experiment, with one major difference. Here we wanted to keep the cerebral temperature constant. As such, the setpoint temperature of the Carotid Arterial Blood Cooling unit was allowed to vary. The setpoint temperature of the cooling unit was controlled in a loop and was based on the temperature of the venous blood returning from the brain. Our objective was to keep the average cerebral temperature constant at 37.6° C., which corresponds to roughly a venous blood temperature returning from the brain of 37.3° C. A control loop was implemented where if the temperature of the venous blood returning from the brain flowing down the internal jugular was greater than 37.3° C. (prior to passing through the Heating Unit), then temperature of the setpoint temperature of the Carotid Arterial Blood Cooling Unit was decreased by 0.02° C. The update rate was every 2 minutes. Conversely, if the venous blood temperature was below 37.3° C., the setpoint temperature of the Carotid Arterial Blood Cooling unit was increased by 0.02° C. This is a very simple control system, but given the very slow rates of change of temperature, it was able to very accurately track and keep the Cerebral Temperature constant at 37.6° C.

FIG. 9 shows the key temperatures associated with this experiment. In the previous experiment the Carotid Arterial Blood temperature was regulated to 37° C. throughout the procedure and the Cerebral Temperature increased from 37.6° C. (start temperature with a core body temperature of 37° C.) to 38.09° C. when the Core Body temperature reach 41.9° C. The slight increase in Cerebral Temperature is a result of warm arterial blood flowing up the Vertebral arteries. In this procedure however, the Carotid Arterial Blood temperature was gradually regulated to a lower temperature of 36.45° C., which resulted in an average Cerebral temperature of 37.6° C., even when the Core Body Temperature had risen to 41.9° C. From the perspective of the Hypothalamus, the temperature of the patient has remained relatively constant throughout the procedure.

It is interesting to consider that by regulating the temperature of the arterial blood flowing up the carotid to a slightly lower temperature, it would be possible to make the patient feel chilly, and have a desire to remain warm, despite the fact that his core temperature from the neck down is significantly above the normal core body temperature of 37° C. Regulating to a slightly lower temperature could be leveraged to make the procedure more comfortable for patients' if/when human trials are conducted.

FIG. 10 shows all the heat exchange parameters associated with this experiment. They are very similar to the experiment above and will not be discussed in detail. The only real notable differences is that the thermal load on the Carotid Cooling Unit is slightly larger since we are regulating the arterial blood to a slightly lower temperature, and similarly the thermal load on the Jugular Heating Unit is also slightly larger because the Outlet temperature of 43° C. is constant, but the inlet temperature is lower than in the previous case, hence more heat needs to be added to the venous blood.

Experiment C:

This procedure is designed to expose the patient to two temperature plateaus. The first plateau will be at 44° C. for a period of 4 hours, after which the patients core body temperature will be allowed to drop to 42° C., where it will be maintained until a total of 12 hours have elapsed. The purpose of this profile is to leverage the Step Down phenomena which has been observed clinically during whole body hyperthermia trials, where the cells of cancerous tissue is sensitized to heat by being previously exposed to an elevated temperature.

Further, an Infra Red Heating system which generates long wavelength IR radiation has been added to the setup. Long wavelength infra red has been found to be well suited for the induction of hyperthermia since this frequency of light penetrates deep into the skins and the heat flux is distributed across a fairly thick layer of tissue, which helps prevent burns. The IR lamps are capable of inducing up to 1000 W of heat to the patient, and are controlled by a Proportional Control System which gradually decreases the radiation output as the Core Body Temperature of the patient approaches the desired temperature. Once the desired temperature is achieved, the lamps shut off. If the temperature drops below the desired level, the lamps are turned back on until the core body temperature returns to the setpoint, which results in an ON/Off cycling of the IR lamps once the target temperature has been achieved.

System Setup:

The Arterial cooling units will be installed on both the left and right internal carotid arteries to maintain the brain at a relatively cooler temperature, compared to the hyperthermic temperature to which the patient will be exposed from the neck down.

- Arterial pressure on the Internal Carotid arteries will be increase slightly above the patient's normal arterial pressure, to favour blood flow through the carotid arteries as opposed to the vertebral/basilar arteries.
- In this case the blood flowing up the Internal Carotid will be regulated to be at a temperature of about 37° C. or lower. The exact temperature will be controlled by a loop which seeks to maintain the venous blood returning from the brain, through the internal jugular, at approximately 37.3° C. The update rate of the control loop is once every 60 seconds. If the temperature of the venous blood flowing down the internal jugular was above 37.3° C., the setpoint of the Arterial Blood Cooling Unit was decreased by 0.05° C. Conversely, if the temperature of the blood flowing down the internal jugular was lower than 37.3° C., the setpoint of the Arterial Blood Cooling Unit was increased by 0.05° C.

The Heating Units were installed on the Internal Jugular veins.

- The Heating Unit will warm the blood flowing down the Internal Jugular vein to be at about 43.75° C. during the initial 4 hours plateau where we are targeting a Core Body temperature of 44° C. from the neck down.
- The setpoint will be decreased to 41.75° C. during the second plateau (from hours 4-12) during which the desired Core Body temperature is 42° C. from the neck down.
- After 12 hours, blood will stop being pumped through the heating units and it will be allowed to flow naturally down the internal jugular back to the heart. This will have a cooling effect on the patient since the blood will be at a temperature of approximately 37.3° C. (Cerebral Temperature −0.3° C.)

Infrared Heating Lamps were placed around the patient with an estimated maximum heating capacity of 1000 Watts. Long Wavelength Infra-Red is preferred since it penetrates more deeply into the skin and is therefore more easily absorbed and transported by the vascular system.

- The Power Output of the IR lamps was controlled by a proportional control system.
- At a Core Body temperature of 37° C., the lamps generated the maximum output of 1000 W. 1000 W is considered to be adequate to achieved the rise time we desire of approximately 1 hour, but it is not so high that it will cause burns to the skin.
- As the Core Body temperature increased towards the setpoint of 44° C. or 42° C. (depending on the time) the Power Output of the lamps was decreased. This is important to prevent burns since the surface temperature could become quite high as the core body temperature increases to 44° C. in conjunction with being exposed to 1000 W of IR radiation.
- Once the target temperature is achieved, the IR lamps go into an ON/OFF pattern in an attempt to maintain the patient at the target therapeutic core body temperature from the neck down.

After 12 hours the patient will be allowed to cool back down to a normal Core body temperature, during which time the Arterial Blood Cooling Units will continue to regulate the temperature of the blood flowing up the Internal Carotid to a temperature necessary to maintain the cerebral temperature at approximately 37.6° C.

The patient's skin will remain uncovered since the IR radiation must be absorbed by the skin. To limit heat loss to the environment, the patient may be placed in an incubation tent. It is possible that at an elevated core body temperature the patients basal metabolism will be greater than his rate of heat loss to the environment, at which point the patients core body temperature may continue to rise above the desired core body temperature. For this reason, the temperature of the incubation tent should be sufficiently low so that his rate of heat loss to the environment is greater than his basal metabolism.

Experimental Results and Discussion:

The key temperatures which were tracked during the experiment can be seen in FIG. 11, and the key heat transfer parameters are plotted in FIG. 12. The combined heating effects of the IR Lamps and the Jugular Heating Units was able to increase the patients core body temperature from 37° C., up to 44° C., in less than 1 hour. During this time period the heat output of the IR lamps started at approximately 1000 W and gradually decreased to about 200 W when the Core body temperature reached 44° C., after which they went into an On/Off cycle as expected as the core body temperature dropped below, or rose above, the setpoint temperature respectively. During this time the Jugular Heating Units were regulating the venous blood to 43.75° C.

After 4 hours, the setpoint temperature of the IR lamps was decreased to 42° C., as the regulation temperature to which the venous blood was heated by the Jugular Heating Units was decreased to 41.75° C. Over the course of 1.7 hours the patients core body temperature fell from 44° C. to 42° C. During this cooling phase the IR lamps remained off since the patients core body temperature was above the desired setpoint temperature of 42° C. Once the core body temperature dropped below 42° C., at approximately t=5.7 hrs, the IR lamps resumed their ON/Off modulation and stabilized the patients core body temperature to the desired 42° C. After 12 hours, the IR lamps were shut off and the Jugular Heating Units were disconnected, and the patient was allowed to cool back down to a normal core body temperature. After 3 hours of cooling the patient had returned to a comparatively normal core body temperature of 37.6° C.

Throughout the procedure, the Arterial Cooling Units were used to regulate the temperature of the arterial blood flowing up the internal carotid arteries, to the brain, in such a way as to keep the Cerebral temperature constant at approximately 37.6° C. The temperature of the venous blood returning from the brain, in the Internal Jugular vein, was monitored prior to being pumped through the Jugular Vein Heating Unit. The mean Cerebral temperature is assumed to be approximately equal to the Jugular Vein Blood Temperature +0.3° C. If the temperature of the venous blood in the Internal Jugular rose above 37.3° C., the setpoint of the Arterial Cooling Unit on the Internal Carotid was decreased by 0.05° C., and conversely if the venous blood temperature fell below 37.3° C., the setpoint of the Cooling Unit was increased by 0.05° C. The update rate of the control system was decreased to 60 seconds compared to the previous experiment, and the temperature increment increased to 0.05° C. from 0.02° C. in order to increase the response time of the control loop, to track the more aggressive slew rates which are introduced by the IR lamps.

Throughout the procedure we were successful in making the patients core body temperature follow a desired therapeutic profile, all the while maintaining the brain at a lower temperature, and in this case keeping it at a very nearly constant temperature such that the hypothalamus is effectively unaware that the core body temperature from the neck down is being exposed to elevate hyperthermic temperatures.

Experiment D:

This experiment is identical to Experiment C with one key exception. Over the coarse of the procedure we decrease the Cerebral temperature by 1° C. During the initial hour the Cerebral temperature is decreased from the initial value of 37.6° C., down to 36.6° C. and it is maintained at this value for the full 12 hour duration. After the 12 hour period, the cerebral temperature is gradually increased back to its normal value of 37.6° C. The cerebral temperature is modified by controlling the temperature of the arterial blood flowing up the internal carotid. The cerebral temperature is monitored like before, by measuring the blood temperature returning from the brain in the internal jugular vein. In this particular experiment, the arterial blood is cooled to a temperature as low as 35.1° C. to achieve the desired cerebral temperature of 36.6° C. It is assume that 10% of the cerebral blood supply is coming form the vertebral arteries, and enters the brain at the core body temperature which in this case was as high as 44° C. The key temperature and heat transfer profiles for this experiment are plotted in FIGS. 13 and 14 respectively.

There are several benefits to regulating the cerebral temperature to a lower value. A first is that the hypothalamus will experience a temperature lower than its desired set point and as a result the patient will feel chilly and will enjoy the warming effect of the IR lamps. A second benefit is that the patient will not sweat which would result in dehydration and discomfort over a prolonged period. In essence the patient will feel similar to the early stages of a fever when the core body temperature is rising. Although the body temperature is rising, it is below the desired level that the hypothalamus is trying to achieve, and as a result the sympathetic nervous system responds as though the patient were feeling chilly, despite the elevated core body temperature. In this case we are exposing the hypothalamus to a temperature which is lower than its desired set-point, despite the elevated core body temperature from the neck down, and as a result the sympathetic nervous system responds by trying to warm the body.

Another benefit is that the lower temperature will have a preserving effect on the brain, and will help offset any hotspots which might be generated by having warm arterial blood entering the brain through the vertebral/basilar arteries. Cool temperatures in this range will not damage the brain, but excessively hot temperatures can.

Scenario E:

In this scenario we are attempting to reach an elevated temperature of 46° C., for several minutes, in order to kill a virus, bacteria or other disease which has been found to respond to such an elevated temperature. For example, the HIV virus has been shown to die, in vivo, if a sufficiently high temperature can be achieved. Given that the human body cannot be exposed to temperatures of 46° C. for extended periods of time, it is desirable to heat the patient very rapidly to the desired temperature, maintain the temperature for just enough time to kill the virus or bacteria, and then to return the core body temperature back down to a more tolerable level rapidly.

System Setup:

In order to heat the patient very rapidly, the patient will be immersed in a bath of water at 47° C. Rapid heating and cooling is necessary since we want to achieve the target temperature for a very specific duration, but we want to reduce the amount of time the patient is exposed to elevated temperature during the warm up and cool down cycle.

The Arterial cooling units will be installed on both the left and right internal carotid arteries to maintain the brain at a relatively cooler temperature.

Arterial pressure on the Internal Carotid arteries will be increase slightly above the patient's normal arterial pressure, to favour blood flow through the carotid arteries as opposed to the vertebral/basilar arteries.

The Heating Units will not be installed on the Internal Jugular veins.

Given that the water bath is capable of transferring large amounts of heat to the patient, the cooling effect of the un-heated blood flowing down the internal jugular is fairly minor.

Secondly, it is beneficial in this case to expose the heart to a slightly lower temperature and hence having the cool blood from the internal jugular mixing with other venous blood will help keep the heart at a slightly lower temperature than the below neck hyperthermic treatment temperature.

Assuming a cardiac output of 5 liter/min with the cervical portion being 1 liter/min, the mean temperature of the blood entering the heart is the weighted average of the blood flow entering the heart at the core body temperature and the blood flow arriving from the jugular vein at the lower temperature.

Once the patient has maintained a core body temperature of 46° C. for 5 minutes, the patient will be immersed in a bath of cool water at 30° C. to bring his core body temperature back to normal more rapidly than if he were allowed to cool in air.

Experimental Results and Discussion:

The temperature of key parameters is plotted in FIG. 15 and the key heat transfer parameters in FIG. 16. At time=0 minute, the patient is immersed in a bath of water at 47° C., from the torso downwards. The water is being circulated by jets to ensure forced convection and excellent heat transfer to the patient. After about 1 minute the core body temperature starts to increase rapidly. At time=5 minutes, the core body temperature has reached 43° C. Given that the majority of the cerebral blood flow is being supplied by the internal carotids, and the blood flowing through the internal carotid is being regulated to approximately 37° C., the cerebral temperature has only increase by 0.6° C., to 38.2° C. compared to the original 37.6° C. At t=13 minutes, the target temperature of 46° C. has been achieved. The cerebral temperature is now at 38.6° C. which is still very reasonable. The increase in cerebral temperature is a function of the ratios of blood flowing through the carotid versus the vertebral arteries. In this case, given that we increased the arterial pressure on the carotid arteries slightly, approximately 90% of the cerebral blood seems to be supplied by the carotid arteries, while about 10% is still being supplied by the vertebral arteries. The average cerebral temperature is therefore approximated by:

$$T_{cerebral} = 0.9 \times T_{carotid} + 0.1 \times T_{vertebral} + 0.6° C.,$$

where the 0.6° C. is the assumed temperature differential between arterial blood and the brain.

In this case, $T_{carotid}$ is maintained at approximately 37° C., while $T_{vertebral}$ increase in proportion to the rise in core body temperature, and is effectively at approximately 46° C. after 13 minutes. The result is an average cerebral temperature of 38.6° C. which is well within acceptable limits. If desired, the blood flowing through the arterial cooling unit, could be decreased to a temperature of say 36° C., which would result in a Tcerebral of exactly 37.6° C., which is normal.

The temperature of the blood flowing down the internal jugular vein, closely track the average cerebral temperature, with a small negative offset. Given that the primary method of removing heat generated by the brain is by transferring heat to the cerebral blood flow, the brain is typically about 0.3° C. warmer than the venous blood flowing out of the brain.

The temperature of the blood flowing out of the Arterial Blood Cooling Unit (100) is kept very near to 37° C. throughout the procedure. After about 7 minutes we begin to see a very small increase in $T_{carotid}$, as a result of the finite gain of the proportional control system used to regulate the temperature of the system. The lag is due to the large thermal capacity of the Sterilized Water bath 106 described earlier. The maximum $T_{carotid}$=37.18° C. is achieved at t=12 minutes.

At t=18 minutes, the core temperature has been maintained at 46° C. for the desired 5 minutes, and the water in the bath is exchanged for cool water at 30° C. to rapidly bring the patient back down to more tolerable temperatures. Within approximately 5 minutes, the patient's core body temperature is back near 38° C., and the water is removed from the bath.

FIG. 16 shows the amount of heat which is transferred to the patient by the various processes. The most dominant mechanism of heat transfer is from the Water Bath to the patient. The maximum transfer of heat is achieved at t=0, when the water temperature is 47° C., while the surface skin temperature is only approximately 34° C. which results in a large temperature differential and hence maximum heat transfer. At the surface temperature of the patient increases, and the core body temperature begins to increase, the temperature of the skin begins to increase and the heat transfer from the warm water bath to the patient begins to decrease. The heat transfer is approximated by:

$$\dot{Q}_{Water}=(T_{water}-T_{skin})*h*A$$

Where:
$T_{water}$=temperature of the water bath
$T_{skin}$=surface temperature of the patients skin
h=effective coefficient of convection from the water bath to the patient
A=surface area of the patient submersed in the water path.

At t=0, we observe a heat transfer rate of approximately of 12 kW, which then begins to decay exponentially as the core body temperature increases and the temperature differential between the water and skin decrease. At t=18 minutes, when cool 30° C. water is introduced into the bath, there is a temperature differential of 16° C. between the patients skin and the water, and hence a very large cooling effect is achieved, and heat is removed from the patient at a rate of 19 kW. The patient's temperature quickly drops to 38° C., and the cool water is removed from the path.

Another dominant heat transfer process is the heat which is removed from the arterial blood by the Arterial Blood Cooling Unit 100. Warm arterial blood at the patient's core body temperature flows into the unit, heat is removed in sufficient quantity to bring the blood back to approximately 37° C. The approximate heat loss can be calculated by:

$$\dot{Q}_{Carotid}=(37° C.-T_{core})*\dot{V}_{Carotid}*\rho*C_p$$

Where:
$\dot{Q}_{Carotid}$ is the rate of heat removal from the arterial blood flowing through the Cooling Unit 100.
$\dot{V}_{Carotid}$ is the blood flow through the unit in ml/sec.
$\rho$ is the density of blood in grams/ml.
$c_p$ is the specific heat of blood in J/g ° C.

The rate of heat removal from the Cooling Unit peaks at t=16.5 minutes, and is 604 Watts, when the core body temperature was at 46.24° C. and the arterial blood was exiting the Cooling Unit 100 at 37.17° C.

There is also a small amount of heat loss to the environment. It is difficult to measure heat loss to the environment, but we estimate that at the peak core temperature, approximate 125 Watts was being lost to the environment, mainly by breathing in cool air, and by having the shoulder, neck and head exposed to ambient air.

The final source of heat that needs to be mentioned is the Basal Metabolism. At room temperature the Basal Metabolism of a typical adult is about 84 Watts, and it increases exponentially as the core body temperature increases to approximately 162 Watts at 41.8° C.

Given that the blood flowing back from the brain through the Internal Jugular was not being re-heated since we did use the Venous Blood Heating Unit 200 in this scenario, the blood reaching the heart is at a slightly lower temperature than the core body temperature. The temperature of the blood entering the blood through the venae cava can be approximated by taking the weighted average of the two blood flows as follows:

$$T_{vanae\_cava}=f_{cervical}*T_{Jugular}+(1-f_{cervical})*T_{Core}$$

Where:
$f_{cervial}$=fraction of the cardiac output which is supplied to the brain. Approx=0.2.
$T_{jugular}$ is the temperature of the venous blood returning from the brain. =38.8° C. at t=16 min.
$T_{core}$ is the core body temperature and we estimate that the non-cervical venous blood returning from other parts of the body is be approximately at the core body temperature.

Using this approximation we find that at t=16 min, the blood entering the heart through the venae cava is at 44.7° C., while the core body temperature is at 46.28° C. Having the heart experience slightly lower temperature than the core body temperature can be beneficial in increasing the achievable core temperatures without overstressing the heart muscle. Furthermore, the blood entering the lungs through the pulmonary artery would also be at this slightly lower temperature of approximately 44.7° C., which help delay the breakdown of the gas-blood barrier in the alveoli.

Finally, if the patient was a male, the scrotum could have been wrapped in a watertight plastic bag, and a small tube of cool water could have been pumped into the bag to ensure that the testicles are not exposed to the 47° C. water but to water at a lower temperature.

In conclusion, in this scenario we were successful in raising the core body temperature of the patient up to 46° C., in 13 minutes, the temperature was maintained at 46° C. for 5 minutes to achieve a desired therapeutic effect, after which the core body temperature was brought back down to 38° C. during a 5 minute cooling period in a cool water bath. The cerebral temperature was maintained at a temperature significantly below the therapeutic hyperthermic temperature, and did not exceed 38.7° C. The arterial blood flowing up the internal carotid was cooled by the Arterial Blood Cooling Unit and was regulated to approximately 37° C. throughout the procedure. The arterial pressure on the carotid artery was increased slightly relative to the vertebral artery to favour blood flow through the carotid, and to drive arterial blood back through the circle of Willis into those areas typically supplied by the vertebral-basilar arteries. The venous blood flowing back from the brain, through the internal jugular, was not re-heated. Although this has a cooling effect on the core body temperature, it is very small compared to the heating effect of the warm water bath. Furthermore, as the cool blood from the internal jugular mixes with other warmer blood returning from other parts of the body, the heart and lungs are exposed to temperatures which are somewhat below the core therapeutic body temperature, which can be beneficial by protecting the heart as well as the lung gas-blood barrier from the elevated core body temperatures and thereby extending the maximum achievable therapeutic temperature.

Experiment F:

This scenario is identical to the one above with two exceptions.

Firstly, in this case, we will add an extra Cooling Unit and use it to cool the Venous Blood returning to the heart. The purpose of doing this is to preferentially cool the venous blood just prior to its return to the heart, to expose the heart as well as the lung blood-gas barrier to substantially lower temperatures than the therapeutic hyperthermic temperature and thereby allow even more aggressive temperature profiles to be implemented without damaging the heart or the lungs.

Secondly, given the elevated hyperthermic temperatures that we are trying to achieve, we will regulate the cerebral temperature to a value lower than the typical normal cerebral temperature of 37.6° C. This will be done in a manner similar to Experiment D, where the arterial blood temperature flowing up the Carotid Arteries is regulated to a value necessary to maintain the venous blood returning from the brain via the Internal Jugular, at a desired temperature. This will help dissipate any area of high temperature which result by having warm arterial blood flowing directly up the vertebral arteries. In this case, prior to immersing the patient in a bath of warm water, the cerebral temperature will have been regulated to a temperature of 36.6° C., which is about 1° C. below a typical cerebral temperature.

System Setup:

In order to heat the patient very rapidly, the patient will be immersed in a bath of water at 47.5° C. Rapid heating and cooling is necessary since we want to achieve the target temperature for a very specific duration, but we want to reduce the amount of time the patient is exposed to elevated temperature during the warm up and cool down cycle.

The Arterial cooling units were installed on both the left and right internal carotid arteries to maintain the brain at a relatively cooler temperature. The temperature of the arterial blood flowing through the unit was regulated by a control system which attempts to maintain the Cerebral temperature at 36.6° C., which is about 1° C. below normal. The feedback to the control system is by measuring the temperature of the venous blood returning from the brain, in the Internal Jugular vein, prior to having the venous blood pass through the Cooling Unit.

Arterial pressure on the Internal Carotid arteries was increased slightly above the patient's normal arterial pressure, to favour blood flow through the carotid arteries as opposed to the vertebral/basilar arteries, and to drive arterial blood through the Circle of Willis from the carotid arteries towards those areas usually supplied by the vertebral-basilar arteries.

The Heating Units will not be installed on the Internal Jugular veins.

Instead, an additional Cooling Unit 100 will be installed on either the Jugular Veins or on a vein of the arm, or a combination circuit where one catheter is on the internal jugular and the other catheter is on a vein of the arm.

In this scenario, the venous blood was cooled to about 30° C., and approximately 1 liter per minute was bypassed through this system to effect a fairly large decrease in the temperature of the blood flowing back to the heart.

Given that the water bath is capable of transferring large amounts of heat to the patient, the cooling effect of the cooled venous blood will not prevent the desired hyperthermic temperature from being achieved.

Secondly, by cooling the venous blood, the blood flowing to the heart in the venae cava as well as to the lungs in the pulmonary artery is cooler than the hyperthermic treatment temperature, which is beneficial in extending the maximum treatment temperature or duration of the treatment without damaging the heart.

In this scenario, given that the heart and the lungs blood-gas barrier was being maintained at a lower temperature, the patient was maintained at 46° C. for a longer period of about 14.5 minutes. Once the desired treatment duration had been achieved, the patient was immersed in a bath of cool water at 30° C. to bring his core body temperature back to normal rapidly.

Experimental Results and Discussion:

Given that many aspects of the experiment are identical to the scenario above, we will focus mainly on the key differences. The key temperatures are shown in FIG. 17 and the key heat transfer parameters are shown in FIG. 18.

In this case, the additional Cooling Unit 100, was fitted onto the Jugular vein. As the core body temperature began to increase above 37° C., venous blood was directed through the additional Cooling Unit and its temperature decreased to approximately 30.1° C. As the core body temperature of the patient increased, eventually substantially all of the blood from the internal jugular vein was being passed through the additional cooling unit. This results in a linearly decreasing temperature of the venous blood flowing down the internal jugular vein from the initial temperature of 36.3 (t=0 min) down to 30.1° C. (t=7 min).

As the cool blood from the internal jugular, mixes with the warm venous blood returning from other parts of the body, the temperature of the blood in the vena cava is considerably lower than the core body temperature. A similar equation that we discussed above holds:

$$T_{vanae\_cava} = f_{cervical} * T_{Jugular} + (1 - f_{cervical}) * T_{Core}$$

In this case, approximately 1 liter per minute is being directed through the additional cooling unit and is being reinjected into the internal jugular at 30.1° C. The cardiac output is approximately 5 liter per minute. As such $f_{cervical} = 0.2$, and at a $T_{Core}$ of 46.6° C. the blood temperature entering the heart through the Venae Cava is only at 43.2° C., which is a very considerable 3.4° C. lower than the Core body temperature. This is beneficial for the heart muscle, as well as the lungs, since the blood flowing through the pulmonary veins towards the alveoli is at a lower temperature than the core body temperature.

The other difference compared to the previous scenario, is that the patient was allowed to remain at 46° C. for a longer period of 14 minutes since the brain, heart and lungs were being preferentially cooled and exposed to temperatures well below 46° C. In this scenario, the cerebral temperature was maintained at a slightly lower temperature than normal, and never exceeded 37° C. despite a very elevated core body temperature of 46.6° C. from the neck down.

The key heat transfer parameters are shown in FIG. 18. In this case, with the exception of Qwater which is used to heat the patient, all other modes of heat transfer are negative and remove heat from the patient, including the cooling unit which is placed on the Internal Jugular vein of the patient.

The Methods and Systems described herein may be used in conjunction with a Membrane Gas Exchanger, or other type of oxygenator, to provide Oxygen to the brain, for example in case of Cardiac Arrest, which can result at elevated hyperthermic temperatures, e.g. above 44° C. The system can also be used in conjunction with a haemodialysis machine in order to adjust or maintain blood chemistry during extended periods of hyperthermic treatment. Both of these systems are well known in the art and can be combined with the proposed method and apparatus. Also, as mentioned above, higher body core temperatures during hyperthermia treatments may allow lower effective doses of therapeutic drugs to be used, or to facilitate diagnostic procedures.

Alternative Embodiments

Preferred embodiments of the apparatus use a small volume bypass loop, so that a relatively small volume of blood needs to be diverted to the bypass loop at any one time, but the heating and/or cooling units provides for high flow rates in the range of 50 to 1000 ml/min, typically about 400 ml/min, and sufficient thermal capacity for rapid cooling or heating of the blood flow, e.g. in the range of about 300 Watts or more. Preferably the heat exchanger in the bypass loop is designed to allow a large surface area for transferring heat while minimizing the internal volume of the heat exchanger. Beneficially, the system is also able to provide blood flow to the brain at a sufficiently high pressure to supply, via the Circle of Willis, regions of the brain normally supplied by the vertebral and basilar arteries. The system may therefore provide effective and rapid cooling of the brain to maintain a temperature differential relative to the core body temperature. Preferably, the system allows for thermal management of blood temperatures in the range from about −7° C. to about +10° C. relative to normal body temperature. The system also provides for rapid warming or cooling back to a target temperature following treatment.

If required, the system may also provide for temperature regulation, by heating or cooling, of the blood flow returning from the brain. Where there is minimal disruption of the normal blood flow, the system also potentially allows for the patient to remain conscious and comfortable, for example, during extended below the neck hyperthermic treatments.

Although embodiments of the invention have been described and illustrated in detail, it will be appreciated that alternative embodiments or variations of methods, systems and apparatus of the invention may be implemented, for example with one or more bypass circuits for cooling of arterial or venous blood flow and one or more by pass circuits for heating of blood flow. Thus, the temperature of blood flow returning to the heart and lungs from the brain, may also be regulated as appropriate to protect these organs from excessive temperatures. Also, systems and apparatus according to other embodiments may be applicable other diagnostic or therapeutic procedures where it is desirable to maintain a normal or near normal brain (cerebral core) temperature relative to below the neck hypothermia) or hyperthermia of other parts of the body.

Although specific arteries and veins have been referred to in the embodiments described above, other suitable blood vessels may be used. For example, reference is made primarily to the internal carotid artery for supplying blood flow to the brain. However, catheters could be placed on potentially either the Common Carotid or the Internal Carotid depending on where the common carotid divides into the internal and external carotids. In some cases, if they divide at a point which is too high in the neck, the catheters would need to be placed on the common carotid since it is accessible. In this case, the processed blood would flow up both the Internal and External carotids. In the latter case, a little extra blood needs to be processed to supply both branches. In other scenario's, the Inlet Catheter might be placed on the Common Carotid, while the Outlet Catheter might be placed on the Internal Carotid, since it is higher up the neck and might be after the division point. Furthermore, the tip of the Outlet Catheter could be pushed up the Carotid artery to a point beyond where the Common Carotid divides such that the cooled blood flows up the Internal Carotid.

When one of the bypass loops is coupled to blood vessels in the arm, leg or torso, it would be up to the medical professional to choose a suitable vessels. For example, in the arm, the larger vessels are the Axillary artery and vein, Brachial artery and vein and the Cephalic artery and vein.

It will also be appreciated, that as in other known blood treatment equipment, additional elements and sensors may be provided for one or more of the bypass loops. e.g. to allow detection and filtration of emboli (clots or bubbles), or ports for introduction into the blood stream of therapeutic or diagnostic agents. Conventional procedures would be used for preparing and priming the bypass loops and removing air bubbles when initiating operation, for example. The system may include, for example additional sensors for monitoring temperature, pressure and flow at other points, and monitoring of parameters indicative of the patient's core body temperature and core cerebral temperature, or other vital signs, as appropriate.

Moreover, while methods according to the embodiments have been described in detail for implementing below the neck hyperthermia treatments, systems and apparatus as described herein potentially also have other applications where it is desirable to rapidly cool the brain relative to the body, and maintain a temperature differential between the cerebral core temperature and the core body temperature.

For example, The Arterial Cooling unit can also be used to rapidly cool the brain, to a state of hypothermia, for preventing or reducing damage to the brain during Cardiac Arrest, or a concussion, or an accident or injury which could deprive the brain of blood flow or oxygen. Connecting an Arterial Cooling Unit to a Carotid artery and cooling the blood supply to the brain results in a rapid temperature decrease of the brain, and may reduce brain damage until the patient can be brought to a hospital and treated.

INDUSTRIAL APPLICABILITY

A system, apparatus and methods are provided for extra-corporeal blood treatment. In particular a blood treatment apparatus and system is provided for differential control of brain temperature and body temperature below the neck, and methods are provided for establishing and maintaining a neck down differential body temperature, while maintaining near normal brain temperatures, to protect the brain from extended or extreme hypothermia or hyperthermia. For example, a first bypass circuit with heat exchanger for brain blood circulation maintains a near normal blood temperature, while a second bypass circuit for below the neck blood circulation provides for thermal treatment to induce a temperature differential, e.g. hyperthermia, relative to brain circulation. Such systems and apparatus have applications, for example, for diagnostic and therapeutic treatments using hyperthermia. Advantageously, treatments of extended duration or at elevated temperatures above 42° C., for example, may be applicable for hyperthermia treatments for cancer, infectious bacterial or viral diseases, while avoiding or reducing detrimental effects to the brain, and other temperature sensitive body tissues.

The differential control of brain temperature and body temperature can also be leveraged to cool the brain to a hypothermic state while the body temperature from the neck down is at or near a normal core body temperature. This application can be useful in preventing brain damage during cardiac arrest, head trauma resulting in concussions, accidents or stroke Although embodiments of the invention have been described and illustrated in detail, it is to be clearly understood that the same is by way of illustration and example only and not to be taken by way of limitation, the scope of the present invention being limited only by the appended claims.

REFERENCES

[1] J. Van der Zee, "Heating the patient: a promising approach?", European Society for Medical Oncology, 2002.
[2] Raaphorst G P, "Fundamental aspects of hyperthermic biology" In Field S B, Hand J W (eds.): An Introduction to the Practical Aspects of Clinical Hyperthermia. London: Taylor and Francis 1990; 10-54.
[3] Jajardo L F, "Pathological effects of hyperthermia in normal tissues." Cancer Res 1984; 44: 4826s-4835s.
[4] K. Alonso et al. "Systemic Hyperthermia in the Treatment of HIV-Related Disseminated Kaposi's Sarcoma." American Journal of Clinical Oncology 17(4), 353-359, 1994.
[5] Yatvin M. "The rationale for hyperthermic treatment of enveloped viral disease. [Abstract]. Proc. Am. Soc. Clin. Hyperthermic Oncology, 1990.
[6] Spire B, Barre-Sinoussi F, Dormont D. "Inactivation of lymphadenopathy associated virus by heat, gamma rays and ultraviolet light" Lancet 1985; 1; 188-9.
[7] McDougal J. S., Martin L. S., Cort Sp., "Thermal invactivation of the acquired immunodeficiency syndrome virus human T lymphotrpic virus III/lymphadenopathy associated virus, with special reference to antihemophilic factor" J. Clinical Investigation, 1985:76:875-80.
[8] Marcial-Vega V., Farzadeegan J., Lee C., "In vitro heat sensitivity on the AIDS virus {Abstract] Proc. Am. Soc. Clin. Hypetherm. Oncol., 1990.
[9] Neville A J, Sauder D N. "Whole body hyperthermia (41-42C) induces interleukin-1 in vivo"., Lymphokine Res 1988:7:201-9.
[10] Taylor M W, Long T, Martinez-Valdez H. et al., "Induction of gamma-interferon activity by elevated temperatures in human B-lymphoblastoid cell lines." Proc. Natl. Acad. Sci. USA 1984:81:4033-8.
[11] E. Kiyathin, "Brain Hyperthermia During Physiological and Pathological Conditions: Causes, Mechanisms, and Functional Implications", Current Neurovascular Research, 2004, 1, 77-90.
[12] A. Fleur van Raamt, Auke P. A. Appelman, Willem P. T. M. Mali, Yolanda vn der Graff "Arterial Blood Flow to the Brain in Patients with Vascular Disease: The SMART Study" Radiology 2006; 240:515-521.

The invention claimed is:

1. A system for extracorporeal blood treatment characterized by:
   i) an arterial blood flow bypass circuit having input means (101) for receiving arterial blood flow from the body and output means (102) for coupling to a left or right or both carotid arterial blood flows to the brain; a first heat exchange means (103) for regulating a temperature of said carotid bypass blood flow to the brain; pump means (104) for controlling a flow rate of said carotid blood flow to the brain; sensor means (114) for monitoring temperature of output blood flows, and
   ii) a second heat exchange means for concurrently heating or cooling the patient from the neck down to a desired temperature
   iii) control means (300) for concurrently monitoring and controlling the arterial blood flow bypass circuit in order to obtain a desired brain temperature and said second heat exchange means in order to obtain a desired core body temperature,
   wherein the second heat exchange means comprises a venous blood flow bypass circuit having input means (501) for receiving venous blood flow from the brain, and output means (502) for coupling to venous blood flow to the body, heat exchanger (103) configured to regulate the temperature of said venous blood flow from the brain before returning it to the body; pump means (104) for controlling a flow rate and pressure of said venous bypass blood flow; sensor means (114) for monitoring temperature of output blood flows, and wherein said control means (300) further provides for controlling temperature and flow rate of the output venous blood flow to the body.

2. A system according to claim 1 wherein the second heat exchange means comprises of one or more of extracorporeal heaters of the blood, infra-red radiation or infra-red lights, a water bath, a water blanket, an incubator, radio frequency radiation, radio waves, inductive blankets.

3. A system according to claim 1 wherein the control means establishes and maintains hypothermia of the brain relative to a normal or near normal core body temperature from the neck down.

4. A system according to claim 1 wherein the control means establishes and maintains neck down hyperthermia relative to a normal or near normal brain temperature for a predetermined treatment time.

5. A system according to claim 1 wherein the control means establishes and maintains a neck down hypothermia relative to a normal or near normal brain temperature for a predetermined treatment time.

6. A system according to claim 1 wherein the cerebral temperature and or core body temperature from the neck down are programmably modulated during a treatment duration.

7. A system according to claim 1 further characterized by: sensor means for receiving data indicative of a core body temperature and a cerebral core temperature, and wherein the control means maintains said required temperature differential between said input arterial blood flow and output carotid blood flow to provide a desired temperature differential between said core body temperature and said cerebral core temperature.

8. A system according to claim 7 characterized in that the control means maintains a temperature differential between said arterial bypass output and venous bypass output to maintain a predetermined temperature differential between a patient's brain temperature and a below the neck core body temperature.

9. A system according to claim 1 wherein input and output means of each respective bypass circuit further comprise catheters and vascular clamps, or balloon catheters, arranged for diverting at least a part of the carotid artery blood flow or internal jugular vein blood flow through the respective bypass circuit.

10. A system according to claim 1 comprising a sensor for monitoring a temperature of the venous blood returning from the brain via an internal jugular vein as an indicator of cerebral temperature and using this temperature to provide feedback to the arterial blood flow bypass circuit temperature controller of the extracorporeal cooling unit for regulating the temperature of the blood delivered to the brain to achieve a desired cerebral temperature.

11. A system according to claim 1 wherein the means for controlling regulates the rate of blood flow through the arterial cooling unit (100) to provide an arterial pressure in the carotid artery at or above a patients mean arterial pressure.

12. A system according to claim 1 wherein, for operation with a catheter of the intake line (401,601) and a catheter of the outlet line (402,602) placed in the carotid artery, the control means is operable to detect a reverse flow between the intake and outlet lines by sensing a decrease in the temperature of the arterial blood entering through the intake line as the flow rate is increased beyond a certain level.

13. A system according to claim 12 operable to regulate the flow rate through the Arterial Cooling Units (400,600) in a range at or above the flow rate required to initiate reverse flow between the intake and outlet lines.

14. A system according to claim 1 wherein the venous blood flow bypass input means is configured to be placed in the jugular vein or the junction of the jugular vein and subclavian vein.

15. Apparatus for extracorporeal blood treatment for thermotherapy comprising:
   i) a cooling unit (100) characterized by an arterial blood flow bypass circuit having an input 101 for receiving arterial blood flow from the body and an output 102 for delivering arterial blood flow to the brain; a pump (104) for pumping blood through the bypass circuit; a heat exchange means (108/106/103) for cooling the blood flow through the bypass circuit;
   ii) a heating unit for concurrently adding heat to the patient from the neck down,
   iii) control means (300/117) for concurrently monitoring and controlling the temperature of the arterial blood flowing through the cooling unit (100) to maintain a desired cerebral temperature as well as monitoring and controlling the heating unit to maintain a desired core body temperature from the neck down,
   wherein the heating unit (500, 700) is characterized by an arterial blood flow bypass circuit having an input (501) for receiving venous blood flow from the brain and an output (502) for delivering venous blood flow to the body; a pump (104) for pumping blood through the bypass circuit; heat exchange means (208/106/103) configured to warm said venous blood flow from the brain before returning it to the body through the bypass circuit; temperature sensors (114) for monitoring temperatures of output blood flows; said control means (300/117) further providing for monitoring and regulating temperature at the output for delivering venous blood flow to the body at a temperature warmer than the input venous blood flow from the brain.

16. Apparatus according to claim 15 where the heating unit comprises one or a more of extracorporeal heaters of the blood, infra-red radiation or infra-red lights, a water bath, a water blanket, an incubator, radio frequency radiation, radio waves, inductive blankets.

17. Apparatus according to claim 15, wherein the control means is operable, while maintaining below the neck hyperthermia at a core body temperature above 42° C., to maintain a temperature differential between the arterial blood flow to the brain and the core body temperature, for maintaining a normal or near normal brain temperature.

18. Apparatus according to claim 17 wherein the cooling unit is capable of receiving input blood flow at 42° C., or more, and cooling arterial blood flow to the brain by at least 5° C.

19. Apparatus according to claim 15 wherein the heat exchanger of one or more of said bypass circuits comprises both heating and cooling elements (108/208) to enable regulation of the temperature of output blood flow to a desired higher or lower temperature relative to the input blood temperature.

20. Apparatus according to claim 15 wherein each respective heating and/or cooling unit has a thermal exchange capacity of at least 100 W.

21. Apparatus according to claim 15 wherein each bypass circuit is capable of delivering flow rates in the range from 50 to 1000 mL/min.

22. Apparatus according to claim 15 operable for maintaining a temperature differential between a core body temperature and a core brain temperature of at least 4° C.

23. Apparatus according to claim 15 wherein the heat exchange means is characterized by a heat exchange block comprising first and second clam shell portions defining a channel between the first and second portions for carrying blood, wherein the width of the cross section is significantly larger than the thickness of the channel in the direction of the heat transfer.

24. Apparatus according to claim 23 wherein the first and second clam shell portions are separable for cleaning and sterilization, to allow the heat exchanger to be re-used.

25. A method for hypothermic treatment using the system of claim 1, characterized by: subjecting the body to a temperature above a normal core body temperature from the neck down for a therapeutic or diagnostic purpose, while maintaining the brain at a temperature lower than the neck down hyperthermic treatment temperature.

26. A method according to claim 25 characterized by extracorporeally cooling blood flowing from the body to the brain via at least one internal carotid artery.

27. A method according to claim 26 further characterized by extracorporeally heating blood returning from the brain to the body via at least one internal jugular vein.

28. A method according to claim 27 further characterized by providing an extracorporeal bypass system wherein the blood returning from the brain through an internal jugular vein is warmed back to a target hyperthermic temperature.

29. A method according to claim 26 where the body is heated using one or more of extracorporeal heaters of the blood, infra-red lights, heating lights, a hot water bath, heating blankets, radio waves, an incubator, inductive blankets.

30. A method according to claim 26 further characterized by maintaining vascular pressure in the internal carotid arteries sufficient that the cooled carotid artery flow to the brain is delivered, via the Circle of Willis, to areas of the brain supplied by vertebral and basilar arteries.

31. A method according to claim 26 comprising estimating the cerebral temperature by measuring a temperature of venous blood returning from the brain through an internal jugular vein, and dependent on said estimated cerebral temperature, regulating a temperature of the cooled blood delivered to the carotid artery.

32. A method according to claim 26 wherein while the body is being exposed to hyperthermic temperatures from the neck down, the temperature of the brain is decreased below its normal temperature in order to protect the brain from warm arterial blood flowing directly through the vertebral and basilar arteries.

33. A method for hypothermic treatment using the system of claim 1, characterized by: heating or cooling at least part of the body to a core body temperature above or below a normal body temperature from the neck down, while maintaining the brain at a relatively normal temperature, comprising: diverting arterial blood flow through an extracorporeal circulatory bypass system comprising a heat exchanger, warming or cooling the blood flow to a target temperature, returning blood at the target temperature to the left or right or both carotid arteries to provide a temperature differential between the core body temperature and cerebral temperature.

34. A method according to claim 33 further characterized by: diverting blood flow returning from the brain to the body through the internal jugular vein through a second extracorporeal bypass, warming or cooling said blood flow to a desired target temperature, returning blood at said target temperature to the jugular vein, or other suitably sized vein in the arms, legs or trunk, for maintaining said core body temperature below the neck.

35. A method according to claim 33 characterized in that the body is heated to a state of hyperthermia below the neck and the carotid blood flow to the brain is cooled.

36. A method according to claim 35 wherein a disease being treated comprises one of a form of cancer, HIV or AIDS a viral or bacterial infection.

37. A method according to claim 36 further comprising administering chemotherapy while the body is in a state of hyperthermia.

38. A method according to claim 35 further comprising localized cooling of one or more of the lungs, spinal cord, testicles and other heat sensitive body parts and tissues.

39. A method according to claim 38 wherein cooling the lungs comprises ventilation with cooled air.

40. A method according to claim 38 wherein cooling of the testicles comprises application of a cool pack or immersion in cool liquid.

41. A method according to claim 38 wherein cooling the spinal cord comprises application of cooling means along the spine in regions of the neck and back.

42. A method according to claim 33 characterized by; maintaining a state of hyperthermia below the neck with core body temperature above 42° C. and cooling the carotid blood flow to the brain to maintain a near normal brain temperature.

43. A method according to claim 34 characterized by cooling said blood returning from the brain for delivery of temperature regulated blood to the heart and lungs.

44. A method according to claim 35 further characterized by maintaining vascular pressure in the internal carotid arteries sufficient that the cooled carotid artery flow to the brain is delivered, via the Circle of Willis, to areas of the brain supplied by vertebral and basilar arteries.

* * * * *